United States Patent
Yang et al.

(10) Patent No.: US 12,016,933 B2
(45) Date of Patent: Jun. 25, 2024

(54) METHOD FOR STIMULATING AXONAL REGENERATION

(71) Applicant: The Hong Kong University of Science and Technology, Hong Kong (CN)

(72) Inventors: Chao Yang, Hong Kong (CN); Xu Wang, Hong Kong (CN); Kai Liu, Hong Kong (CN)

(73) Assignee: THE HONG KONG UNIVERSITY OF SCIENCE AND TECHNOLOGY, Hong Kong (CN)

( * ) Notice: Subject to any disclaimer, the term of this patent is extended or adjusted under 35 U.S.C. 154(b) by 351 days.

(21) Appl. No.: 17/104,714

(22) Filed: Nov. 25, 2020

(65) Prior Publication Data
US 2022/0160897 A1  May 26, 2022

(51) Int. Cl.
| | | |
|---|---|---|
| *A61K 48/00* | (2006.01) | |
| *A61K 31/138* | (2006.01) | |
| *A61K 31/437* | (2006.01) | |
| *A61K 31/5383* | (2006.01) | |
| *A61K 38/00* | (2006.01) | |
| *A61P 25/00* | (2006.01) | |
| *C07K 14/47* | (2006.01) | |
| *C12N 15/113* | (2010.01) | |

(52) U.S. Cl.
CPC ........ *A61K 48/0066* (2013.01); *A61K 31/138* (2013.01); *A61K 31/437* (2013.01); *A61K 31/5383* (2013.01); *A61P 25/00* (2018.01); *C07K 14/4703* (2013.01); *C12N 15/1137* (2013.01); *A61K 38/00* (2013.01); *C12N 2310/141* (2013.01)

(58) Field of Classification Search
CPC ... A61P 25/00; A61K 48/0066; A61K 31/138; A61K 31/437; A61K 31/5383; A61K 38/00; C07K 14/4703; C12N 15/1137; C12N 2310/141
See application file for complete search history.

(56) References Cited

PUBLICATIONS

Yang et al., Rewiring Neuronal Glycerolipid Metabolism Determines the Extent of Axon Regeneration, Jan. 22, 2020, Neuron 104, 276-292. (Year: 2020).*
Clarke et al., "β-Adrenoceptor Blockers Increase Cardiac Sympathetic Innervation by Inhibiting Autoreceptor Suppression of Axon Growth", Journal of Neuroscience Sep. 15, 2010, 30 (37) 12446-12454; DOI: https://doi.org/10.1523/JNEUROSCI.1667-10.2010 (Year: 2010).*

* cited by examiner

*Primary Examiner* — Joseph R Kosack
*Assistant Examiner* — Jed A Kucharczk
(74) *Attorney, Agent, or Firm* — Nath, Goldberg & Meyer; Joshua B. Goldberg

(57) ABSTRACT

A method of promoting axonal regeneration can include directing neuronal lipid synthesis away from triglyceride synthesis and toward phospholipid synthesis. The method can include administering to the patient a therapeutically effective amount of an inhibitor compound selected from the group consisting of a Lipin-1 inhibitor, a diglyceride acyltransferase inhibitor, and combinations thereof or administering a gene editing therapy to the patient that reduces expression of LIPIN1 or a diglyceride acyltransferase gene.

5 Claims, 12 Drawing Sheets
Specification includes a Sequence Listing.

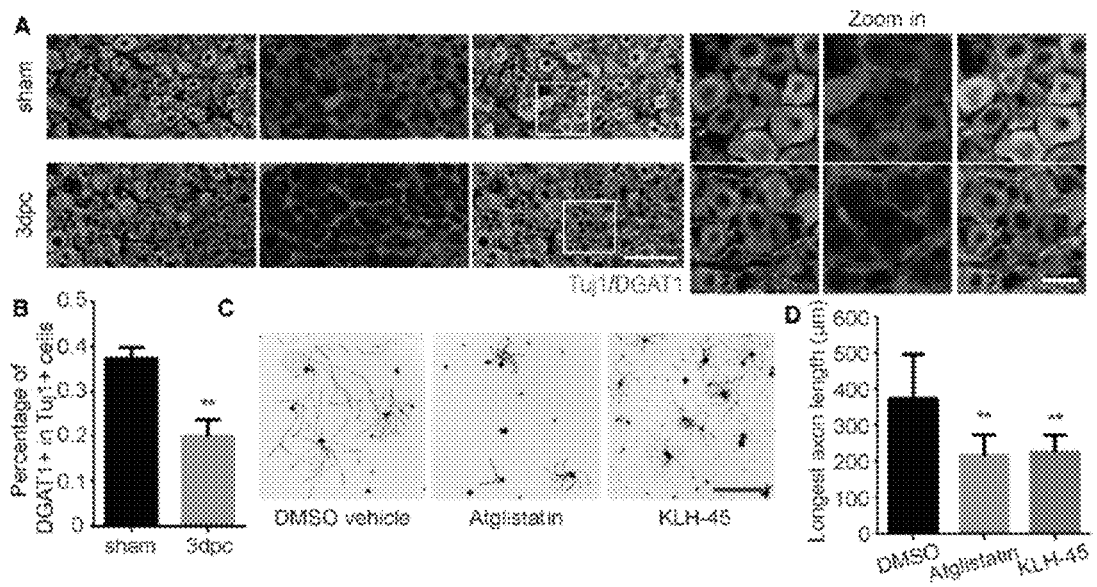
Figs. 7A-7D
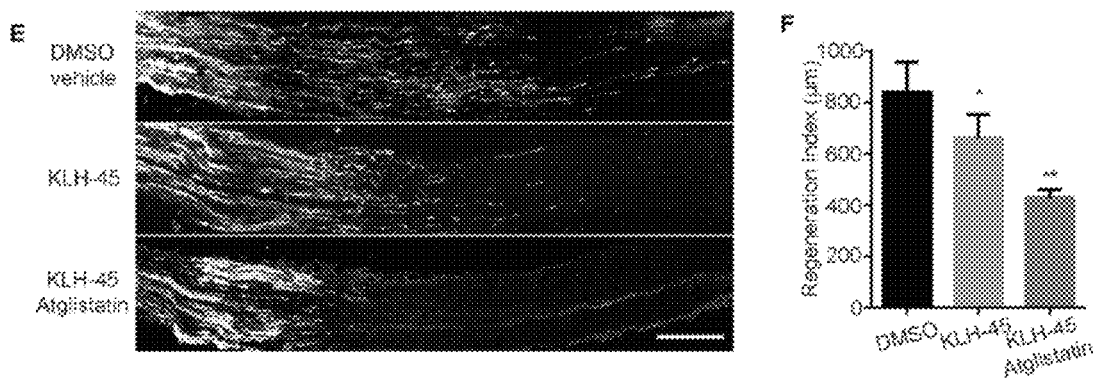
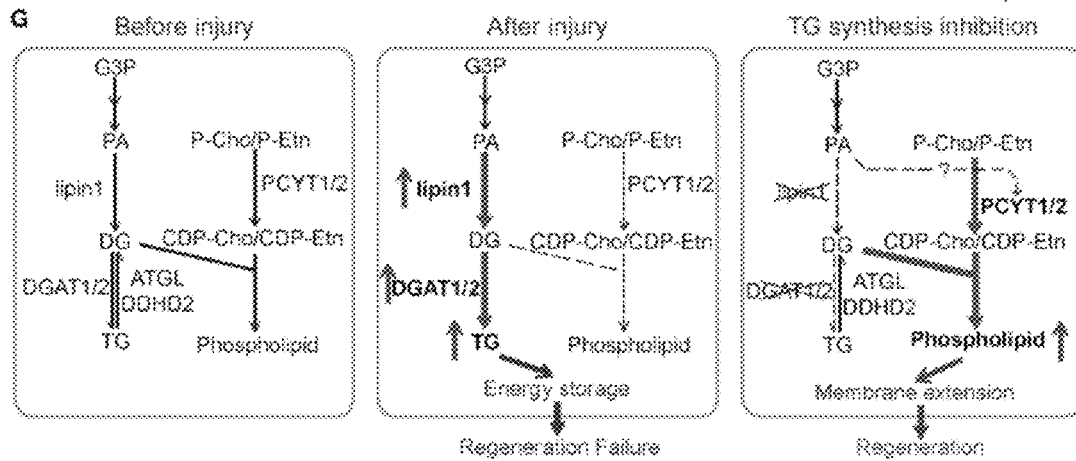
Figs. 7E-7G

METHOD FOR STIMULATING AXONAL REGENERATION

The Sequence Listing submitted in text format (.txt) filed on Nov. 25, 2020, named "Method for Stimulating Axonal Regeneration Sequence Listing.txt", (created on Jan. 11, 2021, 2 KB), is incorporated herein by reference.

FIELD

The present subject matter relates generally to methods and compositions for stimulating axonal regeneration in a patient by modulating glycerolipid metabolism and, particularly, by directing neuronal lipid synthesis away from triglyceride synthesis and toward phospholipid synthesis.

BACKGROUND

Axon regeneration through modulating neuronal intrinsic mechanisms is a very promising strategy to develop potential therapies for neural repair after central nervous system (CNS) injury (Fawcett and Verhaagen, 2018; He and Jin, 2016; Liu et al., 2011; Mahar and Cavalli, 2018).

Understanding the basic biological processes within neurons that actively retard or enhance axon regrowth is becoming increasingly important (Curcio and Bradke, 2018; Goldberg, 2003). Injured neurons require a large supply of lipids for membrane formation as they grow long axons during regeneration (Bradke et al., 2012; Pfenninger, 2009; Vance et al., 2000). Many classes of lipids exist in neurons with various functions, and not necessarily all lipids are crucial for axon growth. Thus, axon regrowth requires coordinated changes in lipid homeostasis in injured neurons.

The metabolism of lipids, such as fatty acids and cholesterol, has been actively studied in the brain (Bazinet and Laye, 2014; Pfrieger and Ungerer, 2011). Recent studies in *Drosophila* larvae sensory neurons indicate that neuronal lipid biosynthesis regulates dendritic complexity (Meltzer et al., 2017; Ziegler et al., 2017). However, relatively little is known about how lipid metabolism is intrinsically regulated in neurons to control axon elongation and regeneration.

Glycerolipids are abundant cellular lipids, including triglycerides (TGs) for energy storage and phospholipids (PLs) for membrane structure. Although TG molecules help organisms survive starvation, they are not regarded as a major direct source of energy for the brain (Schonfeld and Reiser, 2013). However, recent evidence suggests that neuronal TG lipases are very active and that TGs undergo constant turnover in adult neurons (Inloes et al., 2014). TG lipase hydrolyzes a TG to one fatty acid and one diglyceride (DG). DGs are also a precursor of TGs and PLs. Because PLs and TGs share common precursors, neurons likely utilize this strategy to direct the flow of lipids toward membrane production or energy storage depending on needs.

The glycerol phosphate pathway (glycerol 3-phosphate pathway) is an important mechanism for controlling the glycerolipid levels in cells by regulating a series of enzymatic reactions. Lipin1 protein, a phosphatidic acid phosphatase (PAP) enzyme, plays a central role in the penultimate step of the glycerol phosphate pathway and catalyzes the conversion of phosphatidic acid (PA) to DG (Han et al., 2007; Han et al., 2006). In addition, Lipin1 can also regulate gene expression independent of its catalytic function by relocating to the nucleus and acting as a coregulator with transcription factors (Finck et al., 2006). Mutation of Lipin1 causes lipodystrophy with almost complete loss of fat (Harris and Finck, 2011; Reue and Zhang, 2008). In the glycerol phosphate pathway, the final and only committed step is to form a TG by covalently joining a fatty acyl-Coenzyme A (CoA) and a DG molecule. This reaction is catalyzed by two acyl-CoA:diacylglycerol acyltransferase (DGAT) enzymes, DGAT1 and DGAT2, both of which have been implicated in modulating TG homeostasis (Yen et al., 2008). The glycerol phosphate pathway is well characterized in tissues specialized for energy storage or lipid turnover, such as adipose tissue and liver. The function of this metabolic pathway in neuronal response to injury and morphological change, especially in regard to axon growth, has not been explored.

Neurons acquire lipid supplies either through uptake from the external environment or de novo biosynthesis. Regardless of where they are from, lipid building blocks must undergo metabolic processes before they can be utilized by neurons for various functions.

Accordingly, a method of stimulating axonal regeneration overcoming these challenges is highly desirable.

SUMMARY

The present subject matter contemplates a method of and compositions used for stimulating axonal regeneration in a patient by modulating glycerolipid metabolism. Modulating glycerolipid metabolism to promote axonal regeneration can include directing neuronal lipid synthesis away from triglyceride synthesis and toward phospholipid synthesis. In an embodiment, the method includes Lipin-1 depletion to promote axon regrowth. Lipin-1 depletion can promote axon regrowth by regulating triglyceride hydrolysis and phospholipid synthesis. In an embodiment, the method can include directly suppressing triglyceride biosynthesis by inhibiting diglyceride acyltransferase, e.g., DGAT1 and/or DGAT2.

In an embodiment, a method of promoting axon regeneration in a patient can include administering to the patient a therapeutically effective amount of an inhibitor compound selected from the group consisting of a Lipin-1 inhibitor, a diglyceride acyltransferase inhibitor, and combinations thereof. Similarly, the present subject matter contemplates use of a composition for promoting axon regeneration in a patient, or use of a composition in the preparation of a medicament for promoting axon regeneration in a patient, comprising a therapeutically effective amount of an inhibitor compound selected from the group consisting of a Lipin-1 inhibitor, a diglyceride acyltransferase inhibitor, and combinations thereof.

In an embodiment, the method of promoting axon regeneration in a patient can include administering a gene editing therapy to the patient that reduces expression of the Lipin-1 gene or a diglyceride acyltransferase gene. In an embodiment, the axons regenerated are sensory axons. In an embodiment, the axons regenerated are optic or sciatic axons.

BRIEF DESCRIPTION OF DRAWINGS

Various embodiments will now be described in detail with reference to the accompanying drawings.

FIGS. 7A-7G depict (A) DRG sections from WT animals three days after sciatic nerve crush or sham surgery, stained with Tuj1 or DGAT1 antibodies (scale bar: 100 μm) (zoomed-in images are shown in the right panel) (scale bar: 20 μm); (B) percentage of DGAT1+DRG neurons in (A).  P≤0.01, Student's t-test; (C) representative images of DRG neurons in primary cultures treated with DMSO vehicle, Atglistatin (10 μM), or KLH-45 (10 μM). DRG neurites were visualized by Tuj1 staining, scale bar: 400 μm; (D) a graph showing quantification of the length of the longest axon for each DRG neuron in (C), three mice and 10-20 cells from each mouse were quantified in each group,  P≤0.01, ANOVA followed by Dunnett's test; (E) sections of sciatic nerves from WT animals treated with DMSO, KLH-45, or KLH-45 combined with Atglistatin; axons are visualized by SCG10 staining (scale bar: 400 μm; (F) quantification of regenerating sensory axons in (E). ** P≤0.01, * P≤0.05, ANOVA followed by Dunnett's test; and (G) a working model of the glycerol phosphate pathway in axon regeneration with diagrams of glycerolipid metabolism redirection in intact, injured or regenerating neurons.

DETAILED DESCRIPTION

Definitions

Figures 1A, 1B, 1C, 1D, 1E, 1F:
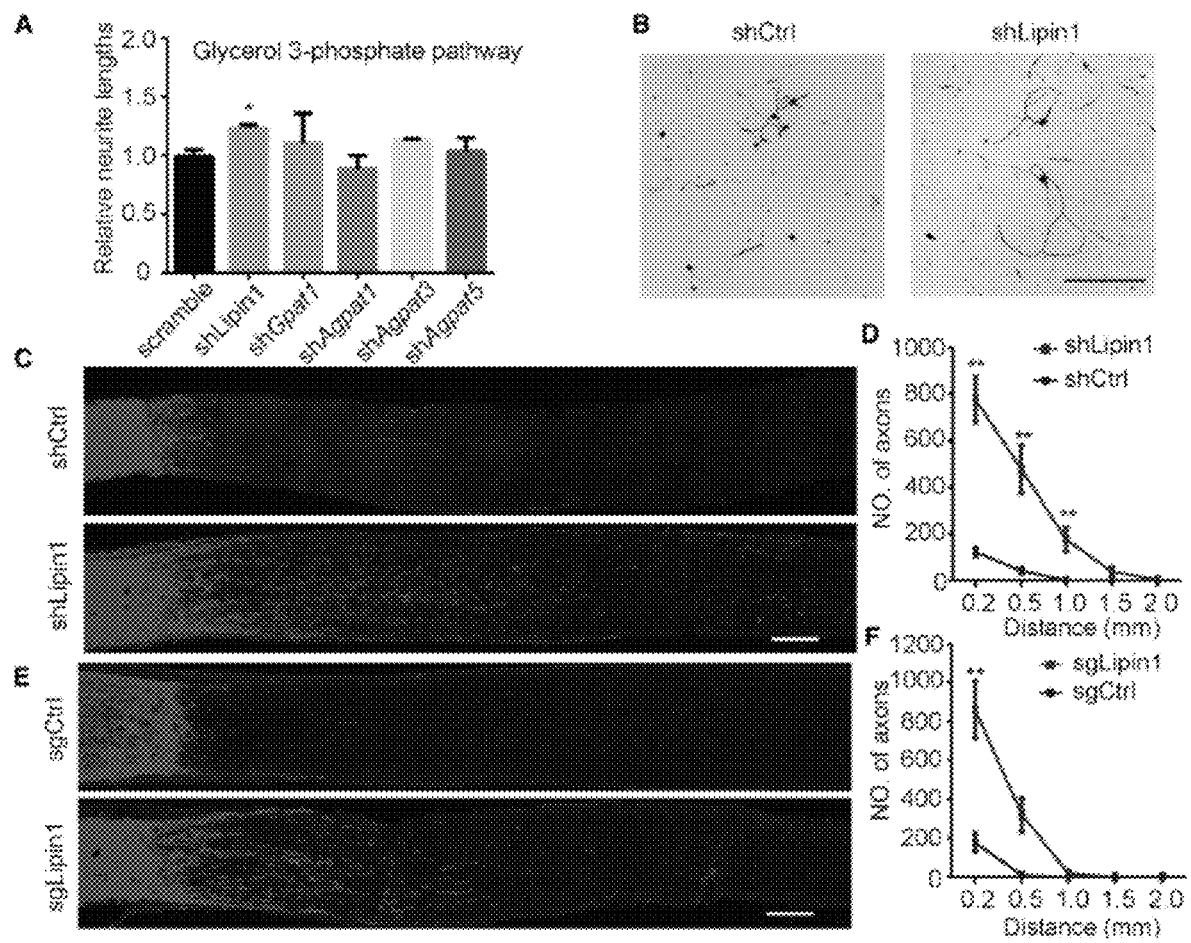
FIGS. 1A-1H depict (A) a graph quantifying axon elongation by in vitro screening of glycerol-3-phosphate (G3P) metabolic genes in adult DRG neurons; (B) representative images of replated neurons from control shRNA and lipin1 shRNA groups with Tuj1 staining, scale bar: 400 µm; (C) sections of optic nerves from WT mice at 2 weeks post injury (WPI), scale bar: 100 µm; (D) a graph depicting the number of regenerating axons at indicated distances distal to the lesion site ($P \leq 0.01$, ANOVA followed by Bonferroni's test, n=6 mice); (E) sections of optic nerves from Rosa26-Cas9 mice at 2 WPI injected with either AAV-control-sgRNA or AAV-lipin1-sgRNA, scale bar: 100 μm; (F) a graph depicting the number of regenerating axons at indicated distances from the lesion site ( P≤0.01, ANOVA followed by Bonferroni's test, n=6 mice); (G) sections of optic nerves from WT mice at 2 WPI injected with AAV-CNTF combined with either AAV-control or lipin1-shRNA, scale bar: 400 μm (zoomed-in images are shown in the lower panel (G'); zoomed-in images are shown in the lower panel, scale bar: 400 m. (G"); zoomed-in images of optic chiasm from (G)) (arrows indicate regenerating axons in optic chiasm, scale bar: 200 μm; and (H) a graph showing the number of regenerating axons at indicated distances distal to the lesion site (** P≤0.01, * P≤0.05, ANOVA followed by Bonferroni's test, n=6 mice, error bars indicate SEM).

The following definitions are provided for the purpose of understanding the present subject matter and for constructing the appended patent claims.

It is noted that, as used in this specification and the appended claims, the singular forms "a", "an", and "the" include plural references unless the context clearly dictates otherwise.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

A "patient," as used herein, refers to a human or animal subject suffering from neuronal injury.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

A method of promoting axon regeneration in a patient can include administering to the patient a therapeutically effective amount of an inhibitor compound or administering a gene editing therapy that results in lowering neuronal triglyceride levels. In an embodiment, the method of promoting axon regeneration in a patient can include administering to the patient a therapeutically effective amount of an inhibitor compound selected from the group consisting of a Lipin-1 inhibitor, a diglyceride acyltransferase inhibitor, and combinations thereof. In an embodiment, a method of promoting axon regeneration in a patient can include administering a gene editing therapy to the patient that reduces expression of the Lipin-1 gene or a diglyceride acyltransferase gene. In an embodiment, the axons regenerated are sensory axons. In an embodiment, paradigastat or A-922500 can be administered to the patient. In an embodiment, a combination of PF-06424439 (10 μM) and PF-04620110 (10 μM) can be administered to the patient. In an embodiment, promoting axon regeneration using gene therapy can include deleting lipin1 or DGATs in RGCs using CRISPR. In an embodiment, the axons regenerated are optic or sciatic axons.

In an embodiment, the Lipin-1 inhibitor compound comprises propranolol hydrochloride, having the following structural formula:

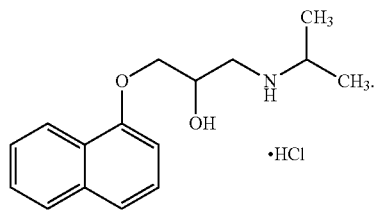 [SMILES: CC(C)NCC(O)COc1cccc2ccccc12 ; Cl]

In an embodiment, the diglyceride acyltransferase inhibitor includes at least one of a diglyceride acyltransferase I (DGAT1) inhibitor and a diglyceride acyltransferase II (DGATII) inhibitor.

In an embodiment the DGAT1 inhibitor includes one or more compounds selected from:

Compound K

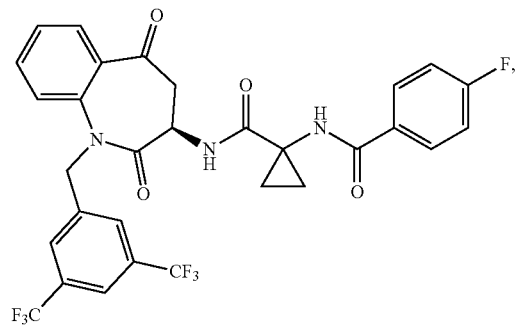

Compound L

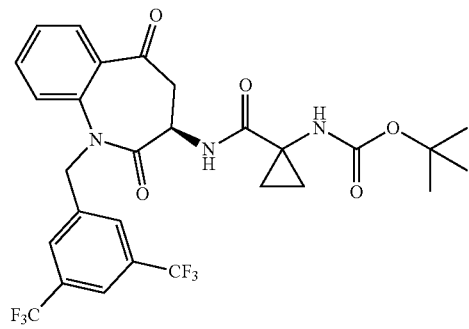

-continued
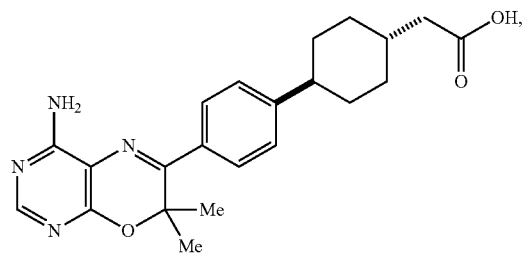
T863
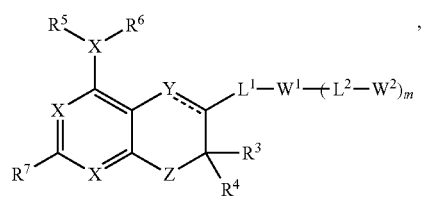
I
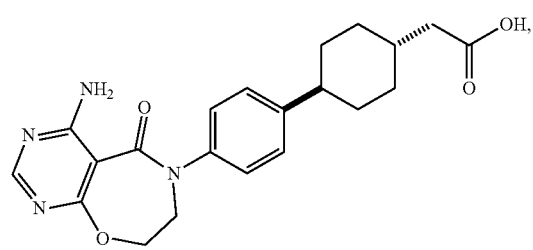
PF-04620110
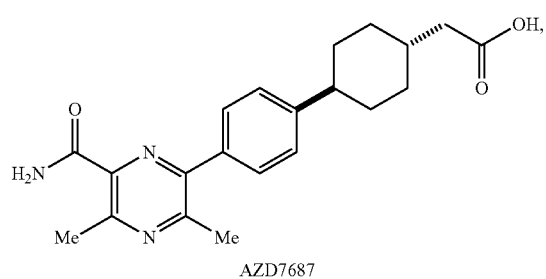
AZD7687
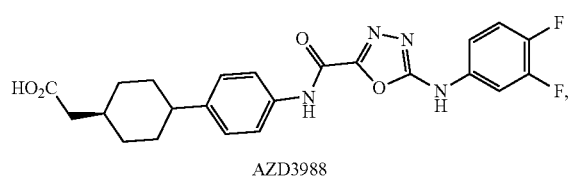
AZD3988
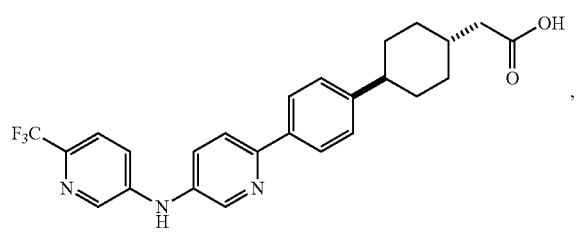
LCQ908
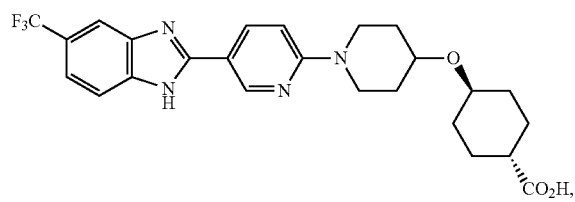
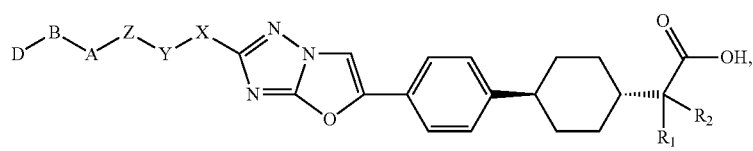
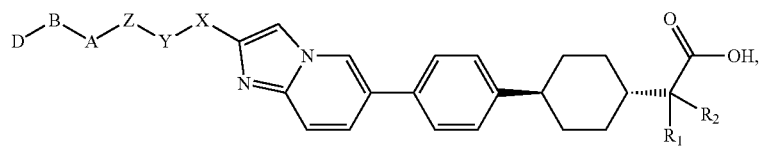
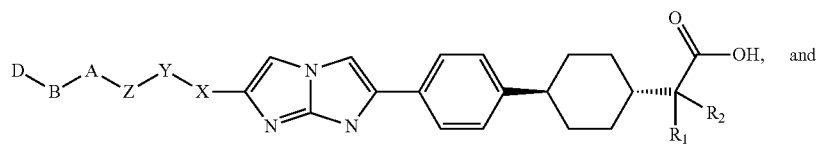
and

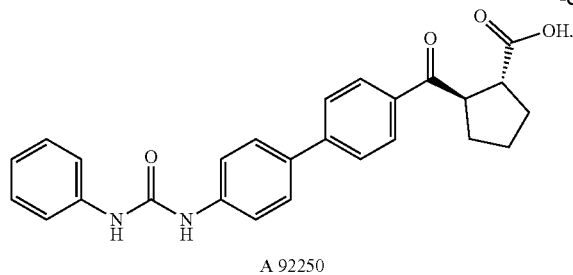
A 92250
In an embodiment, the DGATII inhibitor includes one or more compounds selected from:
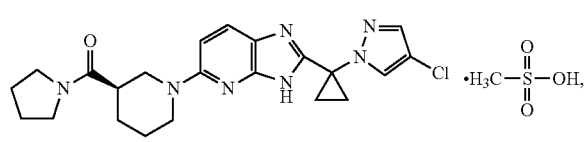
PF-06424439
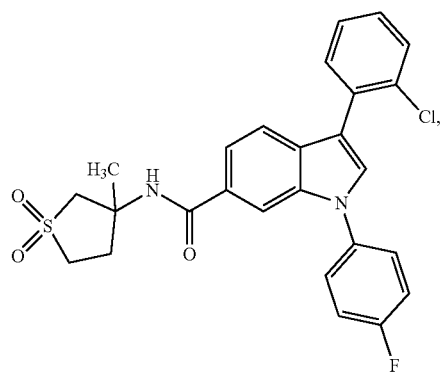
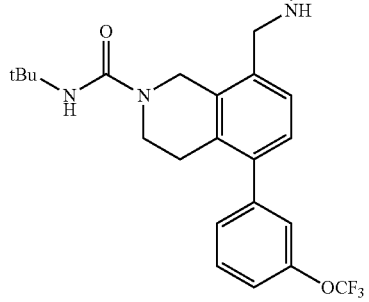
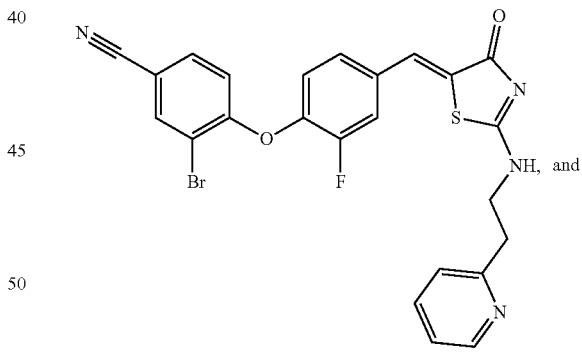
JNJ-DGAT2-A
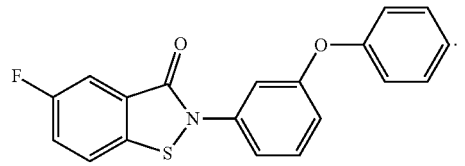
JNJ-DGAT2-B
In an embodiment, the diglyceride acyltransferase inhibitor compound includes one or more compounds selected from:

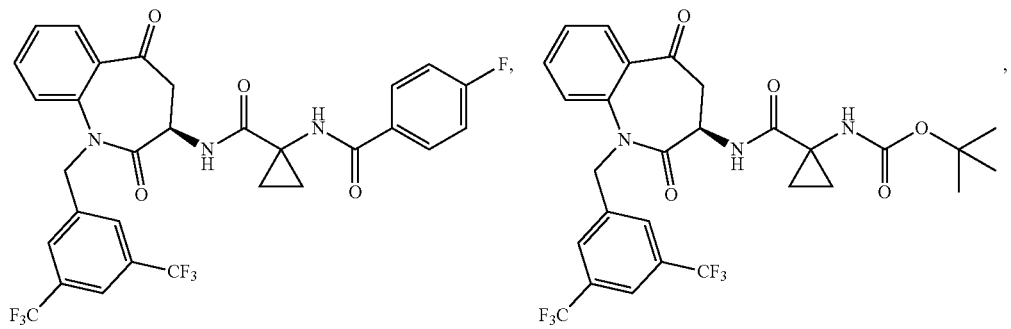
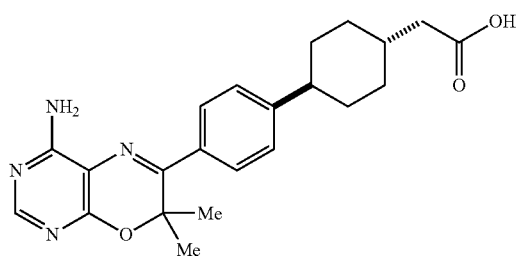
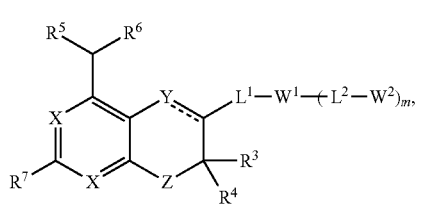
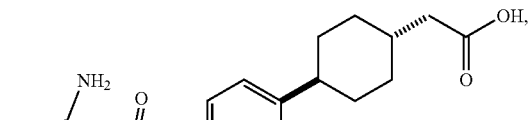
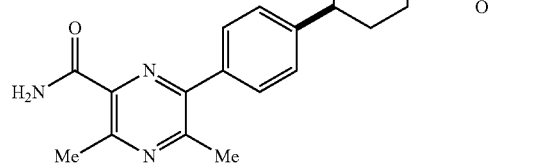
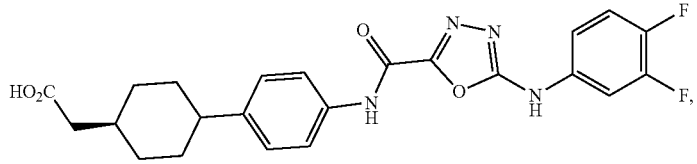
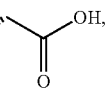
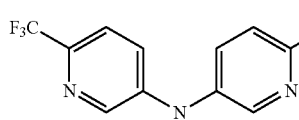
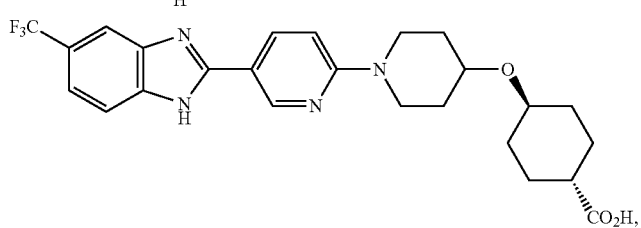

-continued
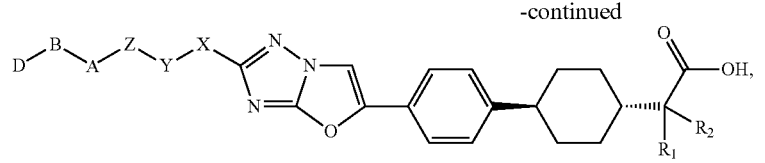
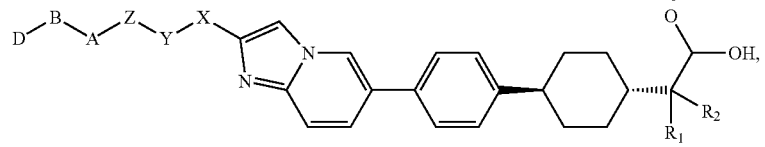
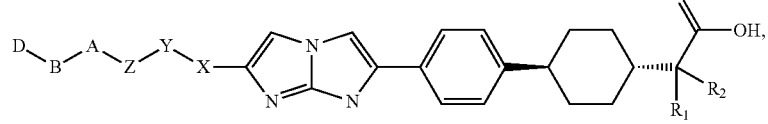
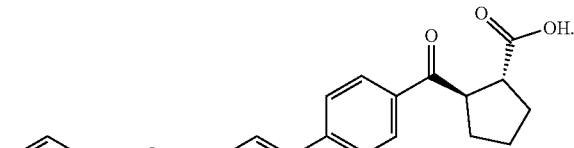
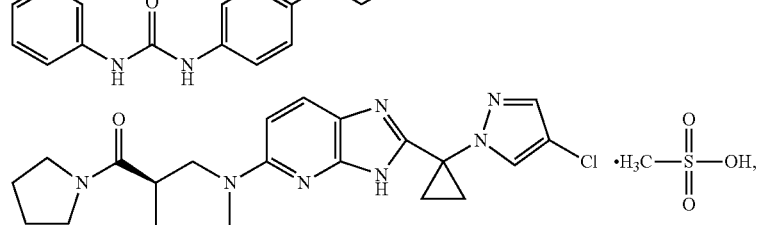
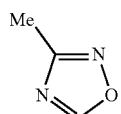
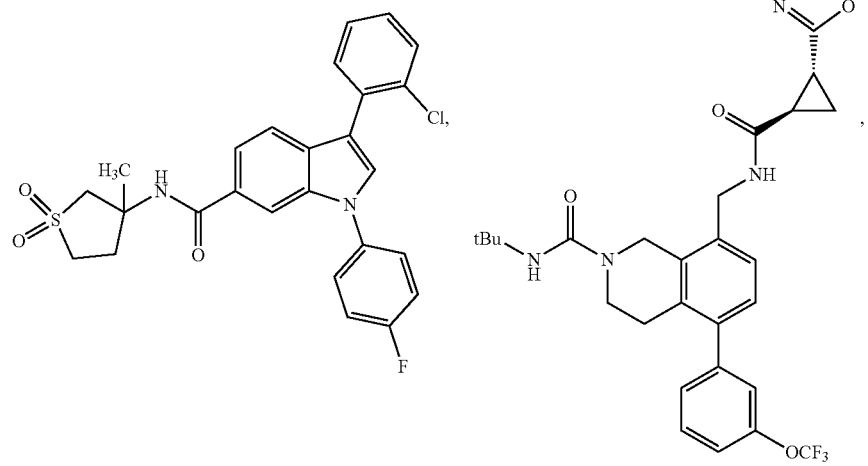
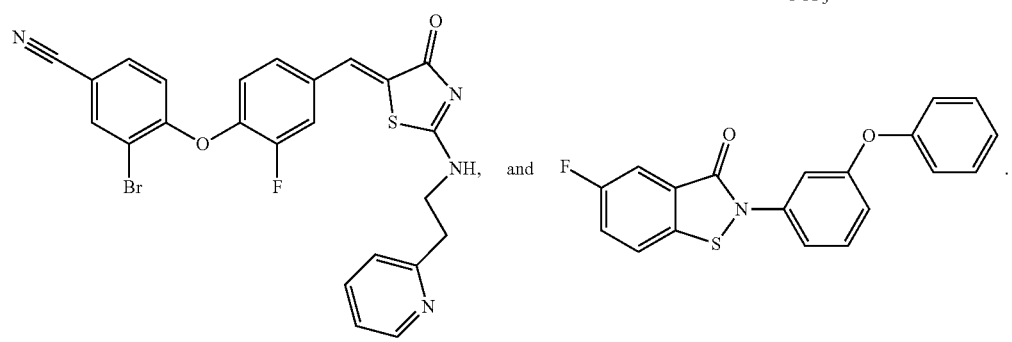

Figure 8A:
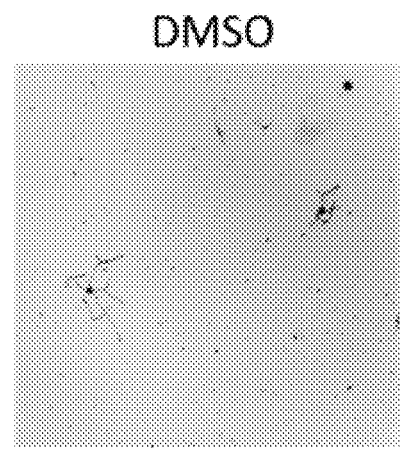
FIGS. 8A-8C depict (A-B) images of cultured dorsal root ganglion neurons without and with the combined inhibitor compounds; and (C) a graph showing the quantification of neurite lengths.
Figure 8B:
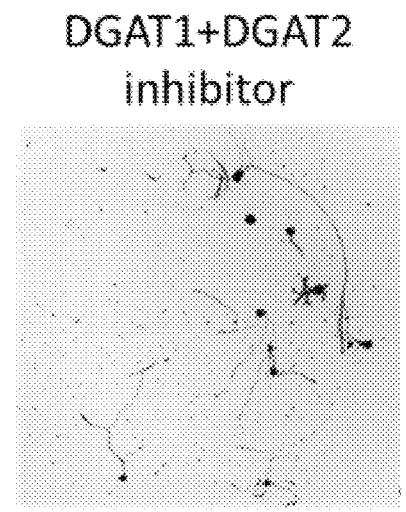
Figure 8C:
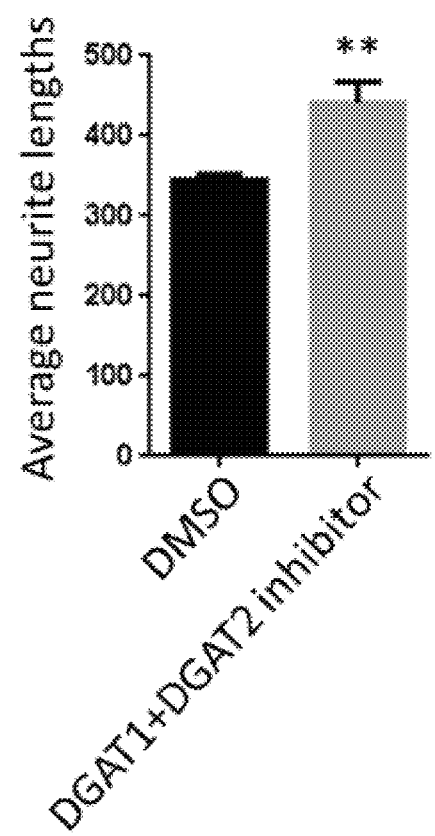
Figure 9A:
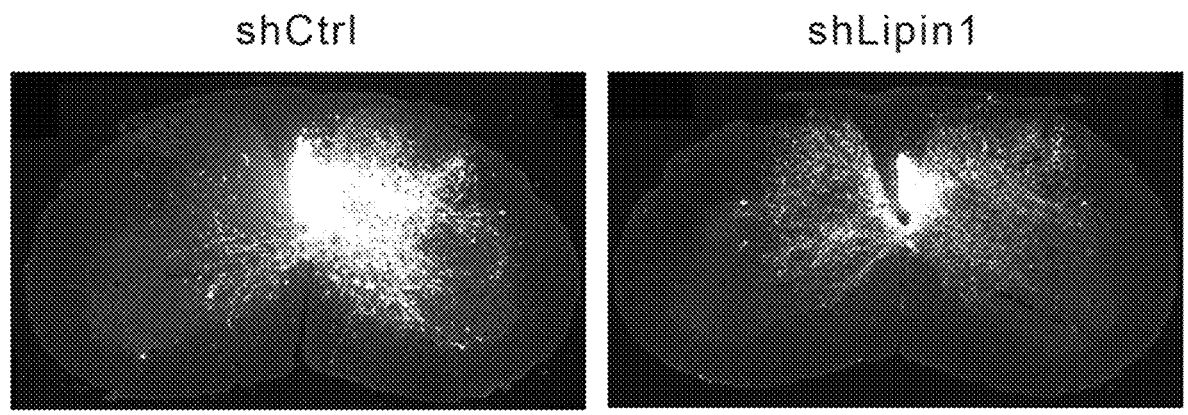
FIGS. 9A-9B depict (A) representative images of cervical 7 spinal cord transverse sections from wild-type mice with pyramidotomy. WT mice were injected with either AAV-control-shRNA or AAV-lipin1-shRNA. AAVs were injected into the right sensorimotor cortex of PI mice; and (B) Quantification of sprouting axon density index. **$P \leq 0.01$.
Figure 9B:
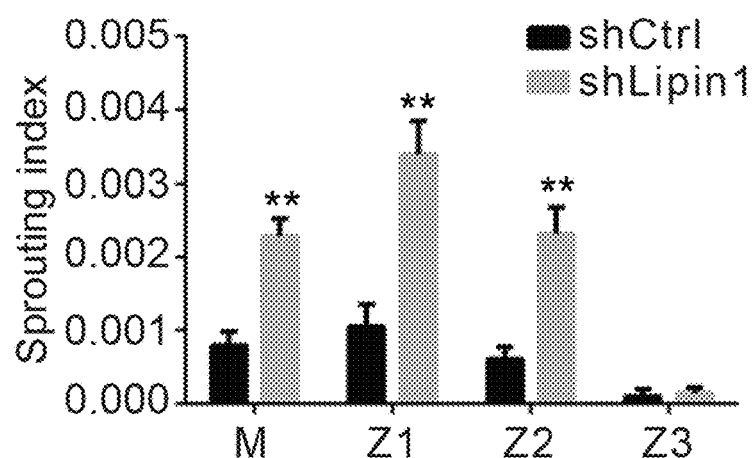

In an embodiment, more than one of the diglyceride acyltransferase inhibitor compounds are administered to the patient. For example, a combination of the DGAT1 inhibitor compound and the DGAT2 inhibitor compound shown below have been demonstrated to promote axon regeneration in an in-vitro culture model (FIGS. 8A-8C). Thus, the following two inhibitor compounds can be administered to the patient in combination

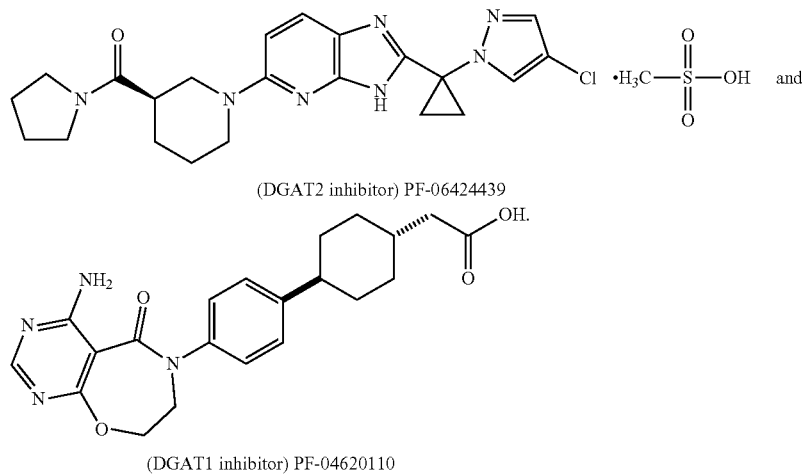

(DGAT2 inhibitor) PF-06424439

(DGAT1 inhibitor) PF-04620110

One or more of the inhibitor compounds can be administered as a pharmaceutical composition in admixture with suitable pharmaceutical salts, buffers, diluents, extenders, excipients and/or carriers (collectively referred to herein as a pharmaceutically acceptable carrier or carrier materials) selected based on the intended form of administration and as consistent with conventional pharmaceutical practices. Depending on the best location for administration, the composition may be formulated to provide, e.g., maximum and/or consistent dosing for the particular form for administration. While the inhibitor compounds may be administered alone, it will generally be provided in a stable salt form mixed with a pharmaceutically acceptable carrier. The carrier may be solid or liquid, depending on the type and/or location of administration selected.

A dosage unit of the composition may include a single inhibitor compound or mixtures thereof with other inhibitor compounds. In one non-limiting example, the composition may be a single dosed ampule or equivalent, or a dropper-bottle that includes the composition and can be provided to the subject in the form of drops. The compounds may be mixed together, may form ionic bonds, or covalent bonds. The composition may be administered in cutaneous, subcutaneous, intraocular, or ocular form, all using dosage forms well known to those of ordinary skill in the pharmaceutical arts. Depending on the particular location or method of drops, serums, elixirs, tinctures, suspensions, syrups, and emulsions may be used to provide the composition of the present invention to a patient in need of therapy for a medical condition or symptom. The composition may also be administered as any one of known salt forms of the compounds or molecules used in the composition.

The present method can include gene therapy inhibition of the Lipin-1 gene, the DGAT1 gene, and/or the DGAT2 gene that includes gene editing/therapy techniques (e.g., CRISPR-Cas9) to knockdown the Lipin-1 gene, the DGAT1 gene and/or the DGAT2 gene.

In an embodiment, an in vivo gene editing therapy for reducing expression of the Lipin-1 gene can include administering to the patient a gene knockdown construct for inhibiting the Lipin-1 gene. The construct can be selected from at least one of an siRNA, a miRNA, an shRNA, an antisense RNA, and an sgRNA. In an embodiment, the method of promoting axon regeneration can include increasing expression levels of ciliary neurotrophic factor in addition to reducing expression of Lipin-1 gene. In an embodiment, the method of promoting axon regeneration can include decreasing expression levels of Pten in addition to reducing expression of the Lipin-1 gene.

In an embodiment, an in vivo gene editing therapy for reducing expression of the diglyceride acyltransferase gene can include administering to the patient a gene knockdown construct for inhibiting the diglyceride acyltransferase gene, the construct being selected from at least one of an siRNA, a miRNA, an shRNA, an antisense RNA, and an sgRNA.

The method of promoting axon regeneration can include modulating glycerolipid metabolism such that neuronal lipid synthesis is directed away from triglyceride synthesis and toward phospholipid synthesis. In an embodiment, the method can include Lipin-1 depletion. Lipin-1 depletion can promote axon regrowth by regulating triglyceride hydrolysis and phospholipid synthesis. In an embodiment, the method can include directly suppressing triglyceride biosynthesis. Directly suppressing triglyceride biosynthesis by inhibiting DGAT1 and/or DGAT2 can promote axon regeneration and reprogram glycerolipid metabolism in the same direction as Lipin-1 depletion.

As described herein, axotomy elevated Lipin-1 in retinal ganglion cells (RGCs), and this upregulation contributed to regeneration failure. In contrast to RGCs, peripheral neurons downregulated DGAT1 upon axotomy, and TG hydrolysis was required for axon regeneration after sciatic nerve injury. Thus, it is believed that TGs may provide lipid precursors to generate PLs for membrane biosynthesis during axon regeneration and that the glycerol phosphate pathway is a potential target for neural repair.

As demonstrated herein, a critical role of the neuronal glycerolipid biosynthesis pathway has been identified in response to injuries and axon regeneration. Previous studies have demonstrated that successful regeneration in neurons requires activation of proregenerative transcription and translation (Cho et al., 2015; Moore et al., 2009; Park et al., 2008; Sun et al., 2011; Terenzio et al., 2018), epigenetic regulation (Cho et al., 2013; Gaub et al., 2010; Oh et al., 2018; Rivieccio et al., 2009; Weng et al., 2017; Weng et al., 2018), cytoskeletal dynamics and transport (Blanquie and Bradke, 2018; Hellal et al., 2011; Nawabi et al., 2015), and mitochondrial mobility and localization (Cartoni et al., 2016; Luo et al., 2016; Zhou et al., 2016), among other processes. The present findings indicate that neuronal lipid metabolism also needs to be properly coordinated for injured axons to regenerate.

Axotomy disrupts the homeostatic synthesis of glycerolipids in the glycerol phosphate pathway by increasing Lipin1 and DGAT1 and limiting axon regeneration in CNS neurons by directing the lipid flux toward energy storage rather than membrane extension (FIG. 7G). Forced Lipin1 depletion reduces the supply for TG production on the one hand and upregulates PA on the other hand which may stimulate PCYT1 activity and subsequent PL synthesis. In addition, active TG hydrolysis generates a supply of DGs as the precursor for PLs. DGAT1 depletion may suppress TG production and drive DGs to the Kennedy pathway, a strategy adopted by peripheral neurons for axon regeneration. It is believed that released free fatty acids from TG hydrolysis may also contribute to the lipid precursor supply through early reaction steps of the glycerol 3-phosphate pathway. It is believed that balanced synthesis between TGs for storing energy and PLs for building membranes may determine axon regeneration.

As demonstrated herein, Lipin1 depletion promoted axon regeneration after optic nerve crush and decreased TGs while increasing PLs in neurons. Directly suppressing de novo synthesis of TG by knocking down Dgat also boosted axon growth and the PL level. The changes in TG and PL levels were more than a simple correlation because either forcing TG storage or inhibiting PL synthesis enzymes almost completely blocked Lipin1- and Dgat1-dependent axon regeneration in vivo. Further, Lipin1 level was reduced in regenerating RGCs induced by either Pten KO or CNTF, two independent mechanisms mediating axon regeneration (Sun et al., 2011). Either Atgl KD or Pcyt1b KD suppressed Pten KO and CNTF-induced axon regeneration. In peripheral nervous system (PNS) neurons that spontaneously regenerate their axons, DGAT1 was downregulated upon axotomy, suggesting that the glycerol phosphate pathway is actively involved in peripheral axon regeneration by shifting lipid storage toward membrane lipid production. Indeed, TG hydrolysis is required for sensory axon regeneration after sciatic nerve crush, indicating that this lipid metabolic pathway affects adult axon regeneration more broadly.

In the plant *Arabidopsis thaliana*, double mutation of pah1 and pah2 (homologues of mammalian Lipin) increases the level of PLs with massive membrane expansion via increased transcription of several PL synthesis genes (Craddock et al., 2015). Studies in yeast show that loss of smp2 (a homologue of mammalian Lipin) promotes the transcription of PL synthesis genes and leads to nuclear membrane expansion (Santos-Rosa et al., 2005). In addition, depleting the PAP activity in rodent enterocytes increases the PC level by increasing PCYT1A protein. It is likely that diminished PAP activity induces PA accumulation, which enhances PCYT1A and possibly other enzymes (Zhang et al., 2019). In mouse neurons, Lipin1 depletion likely promotes PL synthesis through a similar mechanism.

The glycerol phosphate pathway regulates the synthesis of glycerolipids at different growth stages or upon stress. In yeast, membrane lipids are preferentially synthesized from the precursor PA during exponential growth. When cells progress to the stationary phase upon nutrient exhaustion, PA is directed toward TG synthesis. In metabolic cells, the TG represents the major neutral lipids stored in cells and excessively synthesized TGs mainly exist in lipid droplets. The incorporation of synthesized TGs into lipid droplets is a protective mechanism under certain stress conditions. This mechanism can prevent the accumulation of unesterified lipids that may trigger inflammatory responses and cause lipotoxicity in cells.

As demonstrated herein, axonal injury enhanced Lipin1 levels in RGCs, which may have increased TG synthesis. This could be a protective response from RGCs, although it is unclear whether any neuronal lipid droplets were formed. It is challenging to identify neuronal LDs that are rare or transient. Interestingly, in axotomized adult rabbit vagal neurons that regenerate their axons poorly, lipid accumulation can be detected by electron microscopy (Aldskogius, 1978). In other cases, lipid droplets can be detected in axons of *Aplysia*, neurons in the Huntington's disease model, and cortical neurons in culture (Welte, 2015). In the adult mouse brain, LDs are rarely found but can accumulate inside neurons of Ddhd2 KO mice, and also in adult DRG neurons when TG lipase inhibitors were added in culture as shown in our study.

The physiological role of constant and quick turnover of TG inside adult neurons is not entirely clear. The data presented herein suggest that it may be related to supplying membrane lipids. Under injury conditions, it may contribute to rebuilding axons, whereas under naïve conditions, it may be involved in supplying membrane structures such as various vesicles crucial for maintaining normal neuronal functions. However, the possibility that other functions of PLs may contribute to the growth effect cannot be excluded. Further studies will be necessary to elucidate the functional role of TG hydrolysis in neurons.

The endoplasmic reticulum (ER) is the largest organelle and forms a continuous network throughout the neuron including the axon (Gonzalez et al., 2016; Wu et al., 2017). The ER membrane is a major site of lipid biosynthesis, including TG, PC and PE synthesis, and houses many of the enzymes involved (Zhang and Reue, 2017). Axonal injury inevitably causes damages to the tubular ER in the axons. In addition, optic nerve injury induces ER stress in retinal ganglion cells (Hu et al., 2012). Previous studies suggest that the expression of one of the Lipin family members, Lipin2, is induced by ER stress in liver cells (Ryu et al., 2011). Thus, axotomy-induced ER stress in neurons may also affect lipid synthesis through regulating Lipin.

Lipin1 mutant mice have lipodystrophy with significant reduction in fat mass and other pathological defects, which makes Lipin1 a non-ideal translational target. DGAT2 is essential for survival in mice (Stone et al., 2004). However, Dgat1 KO mice are viable, generally lean and resistant to diet-induced obesity (Smith et al., 2000). DGAT1 has emerged as an attractive druggable target for certain metabolic disorders (Chen and Farese, 2005; DeVita and Pinto, 2013).

The present teachings are illustrated by the following examples.

EXAMPLES

Materials and Methods

Figures 2A, 2B, 2C, 2D:
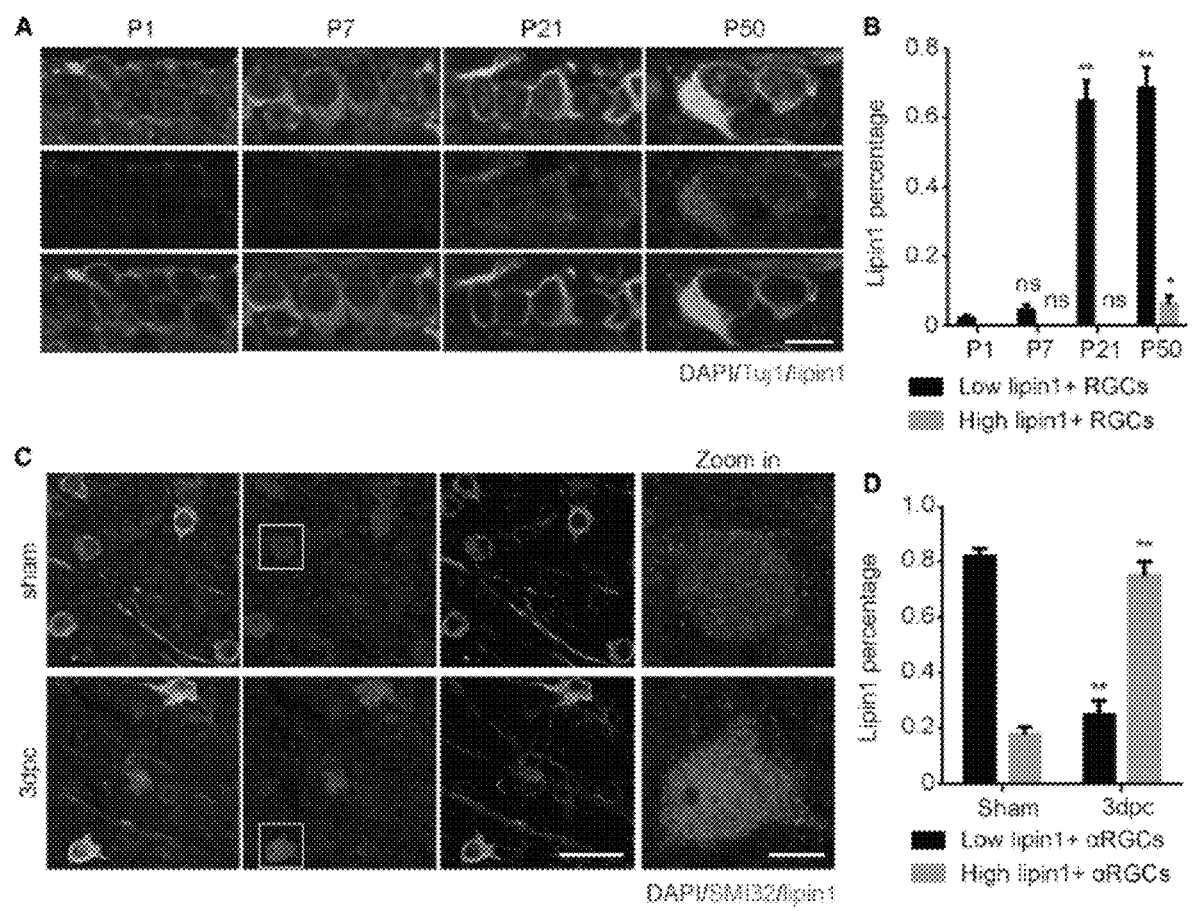
FIGS. 2A-2D depict (A) retinal sections from WT mice of different ages (1, 7, 21 and 50 days postnatal) collected and stained with DAPI (top row), Tuj1 (bottom row) and lipin1 (middle row), scale bar: 10 μm; (B) a graph showing the percentage of RGCs with a low or high lipin1 level at the indicated ages, ** P≤0.01, * P≤0.05, ns, not significant, ANOVA followed by Tukey's test; (C) whole-mount retinas from WT mice three days after axotomy or sham surgery collected and stained for DAPI, SMI32, and lipin1, scale bar: 50 μm (zoomed-in images are shown in the right panel) scale bar: 10 μm; and (D) a graph showing the percentage of αRGCs with a low or high lipin1 level indicated by lipin1 staining (** P≤0.01, ANOVA followed by Bonferroni's test. Error bars indicate SEM).

Wild-type (WT, C57BL/6J, Charles River) mice of both genders at P1, P7 or P50 were used in experiment (FIGS. 2A and 2B). In all other experiments, wild-type and transgenic mice of both genders (7-8 weeks old) were used as indicated. Constitutive SpCas9 knockin mice (stock number: JAX_026179) were obtained from Jackson Laboratories. Opn4-GFP mice were obtained from the Mutant Mouse Regional Resource Center, an NIH funded strain repository, and the strain was donated by the National Institute of Neurological Disorders and Stroke funded Gene Expression Nervous System Atlas (GENSAT) bacterial artificial chromosome (BAC) transgenic project. Pten-floxed mice were gifts from Dr. Zhigang He (Boston Children's Hospital). Housing and breeding conditions followed standard procedures. Experimental and control mice were littermates and were kept together before experiments. All experimental procedures were performed in compliance with animal protocols that were approved by the Animal and Plant Care Facility at the Hong Kong University of Science and Technology.

Cell Lines

Neuro2A cells (ATCC, stock number: CCL-131) were maintained at 37° C. under a humidified 5% $CO_2$ atmosphere using Dulbecco Modified Eagle Medium (DMEM) and supplemented with fetal bovine serum (HyClone). To test the KD efficiency of shRNAs Neuro2A cells were first cultured on a 12-well plate to 70-80% confluency. Cells were then transfected with 1 μg shRNA plasmid by Lipofectamine 3000 for 48 h. The transfection procedure was performed according to the manufacturer's protocol.

Primary Cell Cultures

DRG primary culture and replating were performed as previously described. In brief, for primary culture, L4-L6 DRGs from 7-8 weeks wild-type mice of both genders were dissected and then digested in 0.5% collagenase for 1.5 h. After termination of digestion, DRGs were pipetted 20-30 times in a tube for complete dissociation. Neurobasal-A with B27 as a supplement was used as a medium for DRG culture. Virus was added at 1 day in vitro (DIV1) for genetic manipulation. Atglistatin (10 μM), KLH-45 (1 μM), paradigastat (1 μM) or A-922500 (500 nM) treatment was used for ATGL, DDHD2 or DGAT1 inhibition.

For replating DRG neuron culture, at DIV9-11 of primary DRG culture, cells were gently pipetted on culture dishes. Cells were flushed by 20-30 rounds of pipetting in each well of a 6-well plate. After all the cells were resuspended, they were replated onto a 24-well plate. Fixation and staining were performed 24 h after replating. Tuj1 staining was used to visualize axons and cell bodies of neurons. The lengths of the longest neurites from each DRG neuron were measured manually by NeuronJ in ImageJ. Average lengths of 10-20 neurites from 3 individual mice were used in each group.

For the in vitro screening, dissociated DRG neurons from 4-6 DRGs were first resuspended in 100 μL Amaxa mouse neuron electroporation buffer (Lonza) containing 5 μg respective plasmids. The cell suspension was then transferred to 2 mm cuvette (Lonza) for electroporation. The electroporation was done by using the Amaxa Nucleofector System (Lonza). The primary culture and replating procedures were described previously.

Cortical neurons were cultured as previously described. In short, the cortex from E18 C57/B6 mice of both genders was dissected and digested in 0.5 mg/mL papain for 30 min. Then, 100 μL fetal bovine serum (HyClone) was added to inactivate papain. The cells were then placed into Neurobasal medium (Gibco), supplemented with B27 (Gibco) and 1% penicillin-streptomycin (10,000 U/mL; Gibco). AraC (100 nM; Sigma) was used to inhibit glial proliferation in DIV1-DIV3. After 10 days of culture with AAV-scramble, AAV-shLipin1, AAV-shDgat1 or AAV-shDgat2, cells were harvested, and then TG or PC levels were measured according to the manufacturer's protocol (ab65336 and ab83377).

AAV Construct and Packaging

AAV serotype 2/1 was used for CNTF overexpression. AAV serotype 2/2 was used for all the other overexpression and shRNA AAVs. The AAV construct backbone for overexpression and shRNAs was obtained from Penn Vector Core. qRT-PCR was used for virus titer measurement. The virus titer was $\sim 10^{13}$ GC/mL.

Western Blot

For Western blot analysis, cells were harvested in ice-cold PBS and then lysed in RIPA buffer for 45 min. RIPA buffer consisted of 50 mM Tris·HCl at pH 8.0, 150 mM NaCl, 1% Nonidet P-40, 0.5% Na-deoxycholate, 0.5% SDS supplemented with EDTA-free Complete ULTRA tablets (Roche), and PhosSTOP Complete Easypack (Roche). Cell lysates were centrifuged at 16000 g for 10 min. 4× SDS sample buffer was added to the supernatant of cell lysates. Western blotting was performed according to the standard protocol.

Genomic DNA Extraction and T7E1 Assay

To validate the efficiency of sgRNAs, Neuro2A cells were first cultured on a 12-well plate to 70-80% confluency using Dulbecco Modified Eagle Medium (DMEM) and supplemented with fetal bovine serum (HyClone). Cells were then transfected with 1 μg SpCas9 and respective sgRNA plasmid by Lipofectamine 3000 for 72 h. Genomic DNA of Neuro2A was purified by PureLink™ Genomic DNA Mini Kit. The amplification of target DNA fragment and efficiency testing of individual sgRNAs was performed with manufacturer's protocol of NEB T7 Endonuclease I. Primers used for DNA fragment amplification were listed in STAR Methods. In brief, purified PCR product was denatured and then annealed. If indels existed in the PCR product, heteroduplex DNA would form after annealing. Then T7 Endonuclease 1 was added to recognize and cleave the heteroduplex DNA at the mismatching site. Finally, gel electrophoresis was used to analyze the fragments in the PCR product.

Optic Nerve Injury and Quantification

Intravitreous injection and optic nerve injury were performed as previously described. Mice were intravitreously injected with AAV at postnatal day 28 (P28)-P42. In brief, mice were anesthetized by one injection of 0.5 mg/g Avertin (Sigma) for each surgery. The edge of the eyelid was clamped with a small artery clamp to expose the conjunctiva. Two microliters of virus were injected gently into each vitreous body using a Hamilton syringe. Meloxicam (1 mg/kg) was injected as analgesia after the operation. Mice with obvious eye inflammation or shrinkage were sacrificed and excluded from further experiments.

Four weeks after virus injection, intraorbital optic nerve crush was performed as previously reported. After the mice were anesthetized and an incision was made on the conjunctiva, the optic nerve was crushed by jeweler's forceps (Dumont #5; Fine Science Tools) for 2 s at 1-2 mm behind the optic disk. To visualize regenerating axons, RGC axons in the optic nerve were anterogradely labeled by 1.5 μL CTB (2 μg/μL, Invitrogen) 13 days after injury.

Whole-mount Tuj1 staining was used to determine the number of surviving RGCs at two weeks after optic nerve crush. The retina was dissected and stained following the previous protocol. Briefly, the retina was washed with 1× PBS three times in a 24-well plate and then incubated with PBS with 4% normal goat serum (NGS) for 30 mins. After incubation with the Tuj1 antibody overnight at room temperature, the retina was washed with PBS three times and incubated with secondary antibody for 1 h. After the tissue was washed with PBS, the retina was mounted onto glass slides, and images were taken under a confocal microscope (Zeiss, LSM Meta710; 40× and 63× objective). For each retina, 12 images were taken from different quarters, which covered the peripheral and central regions of the retina. An individual who was blind to different groups counted the number of Tuj1+RGCs.

To quantify the number of CTB-FITC-traced axons after optic nerve crush, the optic nerve was dissected carefully and placed longitudinally for cryo-section (section thickness: t=8 μm). The serially collected optic nerve tissue was stained with the FITC antibody, mounted onto glass slides and imaged under a confocal microscope (Zeiss, LSM Meta710; 10× objective). Captured images were stitched together by using ImageJ. The images of optic nerve with CTB channel were converted into red and exported. Representative optic nerves were cropped from the stitched images. This process may leave some dashed lines or uneven background around the optic nerve. Five images were taken for each optic nerve. The following formula was used to quantify the number of regenerated axons at different distances from the lesion site: $\Sigma ad = \pi r^2 \times [\text{average axon numbers/mm}]/t$. The r is the radius of the optic nerve at the counting site, and the average axon numbers/mm were determined by the average numbers of (axon numbers)/(nerve width at the counting site) of the five sections. The t is the section thickness (8 μm). Axon numbers were counted by an individual who was blind to different groups.

Retrograde Labeling of Regenerating RGCs

At thirteen days after the optic nerve crush, mice were anesthetized and placed in a stereotaxic holder. The crushed optic nerve was gently exposed, with a pulled-glass micropipette attached to a Hamilton syringe, as FG (100 nL, 5% wt/vol) was slowly added into the optic nerve ~2 mm distal to the lesion site. 1 day later, the animals were sacrificed, and the retinas were dissected for staining.

RGC Isolation and qRT-PCR

For isolating single RGCs by mouth-pipetting, 8 weeks old Opn4-GFP mice received an optic nerve crush or sham injury. Then, micro-Ruby (500 nL, 5% wt/vol. Invitrogen) was slowly injected into the optic nerve. 3 days later, the animals were sacrificed, and the retinas were dissected and digested in 0.5 mg/mL papain for 35 min. Then, fetal bovine serum (HyClone) was added to stop the digestion. After centrifugation, the cells were then suspended into Neurobasal medium for further dissociation into single cell suspensions. With a mouth pipette, GFP positive cells or micro-Ruby positive (red) cells were gently pipetted into a new medium drop. After several times, one cell was pipetted into a tube containing lysis buffer. The cell lysis, RT-PCR and pre-amplification were performed with previously described smart-seq2 protocol (Picelli et al., 2014). Pre-amplified cDNA was used as templates for qRT-PCR.

For isolating GFP or mCherry positive RGCs by FACS, the dissociation was done by the above procedure. Cell sorting was performed with a BD FACSAria III instrument. Dissociated retinal cells were separated based on size (forward scatter) and surface characteristics (side scatter) as well as viability (DAPI staining). Doublets or clots were excluded based on the FSC-H-versus-FSC-A ratio. Retinal cells from control mice without any virus injection were used to set up gates for each experiment. 5000 sorted cells were collected in each replicate and RNA was extracted by RNeasy Mini Kit (Qiagen). Total RNA was reverse transcribed to cDNA by SuperScript, 11 Reverse Transcriptase using manufacturer's protocol.

For qRT-PCR, each sample was run in 2-4 replicates. Gapdh was used as endogenous control. The qRT-PCR was done by manufacturer's protocol of LightCycler 480 SYBR Green I Master.

Intrathecal Injection of AAVs

AAV1-control or Lipin1 shRNA was injected to the cal sac between L5 and L6. Briefly, mice were anesthetized with ketamine/xylazine. An incision was conducted in the middle line. Then dura was exposed by laminectomy. A microforged glass needle was inserted into the median area and 3 μL virus was slowly infused to the spinal cord. The skin was sutured with stainless clip and the mice were placed on a heating pad until awake. The sciatic nerve crush was done 4 weeks after injection.

Sciatic Nerve Injury and Quantification

KLH-45 (30 mg/kg/day) or Atglistatin (40 mg/kg/day) were delivered by intraperitoneal injection for 5 consecutive days before injury and 2 days after injury. The same dosage of DMSO injection was used as a control treatment. Sciatic nerve injury was performed as previously described. Briefly, after an incision was made on the skin at the middle thigh level, muscle was gently dissected to expose the sciatic nerve. Then, the sciatic nerve was crushed for 10 s by forceps (Dumont #2; Fine Science Tools). For the sham group, the sciatic nerve was only exposed but not crushed.

Sciatic nerve sections with SCG10 staining were used to quantify the regeneration index. A column with a width of 50 pixels was drawn at different distances from the lesion center, and the average intensity of SCG10 staining was measured using ImageJ. The distance between the lesion center and the column with half the intensity of the lesion center was considered as the regeneration index.

Immunohistochemistry

For BODIPY staining on cultured DRG neurons, cells were first fixed in 4% PFA for 10 min and permeabilized with 0.1% Triton X-100 in 4% NGS. After cells were blocked, the Tuj1 antibody was applied in blocking buffer and incubated at 4° C. overnight. Coverslips were then washed three times with PBS and incubated with secondary antibodies at room temperature for 2 h. Cells were finally incubated with 200 nM BODIPY (Sigma) in blocking buffer for 30 min before mounting.

For immunostaining of tissue sections, mice were first given a lethal dose of Avertin and perfused with PBS followed by 4% PFA. Retinas, optic nerves or DRGs were dissected and postfixed in 4% PFA for 2 h. Tissue was cryoprotected in 30% sucrose overnight and then embedded into OCT compound (Tissue-Tek) at −80° C. Samples were sectioned at −20° C. (20 μm for retina and 8 μm for nerve and DRG). Tissue sections were then blocked and permeabilized with 0.1% Triton X-100 in 4% NGS. After the samples were blocked, they were incubated in primary antibody diluted by blocking buffer overnight. After the samples were washed 3 times with PBS, the corresponding secondary antibody diluted by blocking buffer was applied. After the samples were mounted on coverslips, they were imaged under a confocal or epifluorescence (Nikon, TE2000) microscope.

Lipid Extraction and UPLC-MS

Lipid extraction was performed using the Folch method. Cortical neurons were lysed in a 2:1 chloroform:methanol mixture. After the upper phase was siphoned, the solvent was dried by line blowing with nitrogen. Lipid extracts were analyzed using a Synapt G2 HDMS mass spectrometer coupled with an ACQUITY UPLC system (Waters, Milford, USA). The UPLC separation was carried out using a Charge Surface Hybrid column (particle size: 1.7 μm; length: 100 mm; i.d.: 2.1 mm). The mobile phase consisted of solvent A (0.1% formic acid in water, v/v) and solvent B (0.1% formic acid in acetonitrile, v/v), each with 10 mM ammonium acetate. The elution gradient conditions were as follows: 0 min, 40% B; 2 min, 43% B; 2-2.1 min, 50% B; 12 min, 54% B; 12.1 min, 70% B; 12.1-18 min, 99% B. The flow rate was 0.2 mL min$^{-1}$, and the injection volume was 2 µL. A two minutes post-run time was set to fully equilibrate the column. Column temperature and sample chamber temperature were set to 55° C. and 6° C., respectively. The source parameters were set as follows: source temperature, 90° C.; desolvation temperature, 400° C.; core gas flow, 20 L h$^{-1}$; cone voltage, 40 V; capillary voltage, 3 kV and 2.5 kV in positive and negative ion modes, respectively. The mass range was set as 50-1200 Da. The collision energy was set as 40 V. Individual lipid species were semiquantified by referencing to spiked internal standards obtained from Avanti Polar Lipids (Alabaster, AL), i.e., PC (16:0-d31/18:1) and TG (16:0/18:0/16:0-d5).

Raw UPLC-ESI-MS data were directly imported to the Progenesis QI software (Waters-Nonlinear) for data processing, including peak picking, alignment (retention time correction), and data normalization. The processed data matrices were imported to the IBM SPSS Statistics software (Version 11.0, SPSS Inc., Chicago, IL, USA) for t-test analysis. The m/z values of ions with p value<0.05 were further exported to the SIMCA 14.1 software for OPLS-DA. From the OPLS-DA, ions with VIP≥1 and fold change between different groups>1.5 were considered as potential biomarkers and were subjected to identification using a database (LIPIDMAPS, Metlin, LipidBlast and HMDB) and MS/MS fragmentation.

Quantification and Statistical Analysis

The number of animals or repeats is described in figure legends. All analyses were conducted using Prism 6 software (GraphPad Software, La Jolla, CA). Student's t-test was used for two-group comparisons, and ANOVA was used for multi-group comparisons. An estimate of variation in each group is indicated by the standard error of mean (SEM). ** P≤0.01, * P≤0.05.

Example 1

Investigating the Role of Lipin1 Axon Regeneration

To investigate the role of neuronal lipid metabolism in axon regrowth, essential genes were systematically knocked down using short hairpin RNA (shRNA) in cultured adult dorsal root ganglion (DRG) neurons (Weng et al., 2018). Testing was conducted to determine candidates for regulating the fatty acid metabolic process, cholesterol synthesis, and glycerol phosphate pathway. Fatty acids in the brain come from fatty acid uptake and synthesis. Fatty acid translocase (CD36) transports long-chain fatty acids through the plasma membrane and has relatively high expression level in the brain (Husemann et al., 2002). The rate-limiting enzymes of fatty acid synthesis are acetyl CoA carboxylases (ACC1 and ACC2) (Wakil, 1989). In the cholesterol synthesis pathway, hydroxymethylglutaryl-CoA synthase (HMGCS) is the most upstream enzyme. It catalyzes the reaction from acetyl CoA to hydroxymethylglutaryl-CoA (HMG-CoA) (Bloch, 1965, 1992). The rate-limiting and reversible step in cholesterol synthesis is the conversion of HMG-CoA to mevalonate by HMG-CoA reductase (HMGCR) (Bloch, 1965, 1992). Another critical gene in the pathway is squalene synthase (FDFT1). It was previously shown that Fdft1 is required for neural development (Tozawa et al., 1999). In the glycerol-3-phosphate pathway, glycerol3-phosphate acyltransferase (GPAT) first converts glycerol-3-phosphate to lysophosphatidic acid. Then, 1-acylglycerol-3-phosphate acyltransferase (AGPAT) catalyzes the conversion from lysophosphatidic acid to phosphatidic acid. Lipin then converts phosphatidic acid to diglyceride (Weiss et al., 1960).

As demonstrated herein, most shRNAs did not affect axon regrowth in vitro. Five genes were tested, including lipin1, Gpat1, Agpat1, Agpat3, Agpat5. Gpat: Glycerol-3-phosphate acyltransferase. Agpat: 1-acyl-sn-glycerol-3-phosphate acyltransferase. Adult DRG neurons were dissociated and transfected with the plasmids for three days. Neurons were then replated and fixed 24 h after replating. DRG neurites were visualized by using Tuj1 staining. Three mice and 10-20 neurons from each mouse were quantified in each group. * P≤0.05, ANOVA followed by Dunnett's test. Only Lipin1 shRNA enhanced axon elongation by 20% (FIGS. 1A and 1B). The optic nerve injury model was used to assess the effect in vivo as previously described (Leon et al., 2000) Adeno-associated virus (AAV) carrying Lipin1 shRNA (shLipin1) targeting SEQ ID NO: 1 was injected into the eyes of adult wild-type (WT) mice to knock down Lipin1 in RGCs. Then, optic nerve crush was performed and axon regeneration was examined two weeks later. The RGC survival rates were comparable between the two groups. The vitreous body was injected with either AAV-control-shRNA or AAV-lipin1-shRNA. Axons were labeled by CTB-FITC. Cholera toxin β subunit (CTB) labeling of the optic nerves showed significantly more regenerated axons in mice injected with AAV-shLipin1 than in mice injected with scrambled shRNA (shCtrl) (FIGS. 1C and 1D), suggesting that Lipin1 plays an inhibitory role in axon regeneration in vivo.

The clustered regularly interspaced short palindromic repeats (CRISPR) technique was next used to knock out Lipin1 in RGCs. Lipin1 single guide RNAs (sgRNAs) were designed targeting SEQ ID NO: 2 and SEQ ID NO: 3 and CRISPR induced genome editing was verified in Neuro2A cells. AAV expressing sgRNAs targeting Lipin1 (sgLipin1) (SEQ ID NO: 2 and SEQ ID NO: 3) with mCherry tag was injected into the eyes of mice constitutively expressing the Cas9 enzyme (Platt et al., 2014). The efficiency of in-vivo gene editing was validated by qRT-PCR using Fluorescence-activated cell sorting (FACS)-isolated mCherry-positive retinal cells. It was found that AAV-sgLipin1 but not AAV expressing sgRNA targeting LacZ (sgCtrl) promoted axon regeneration after injection into Cas9 mice (FIGS. 1E and 1F). AAV-sgLipin1 knocked out Lipin1 in approximately 50% of RGCs.

Figures 1G, 1H:
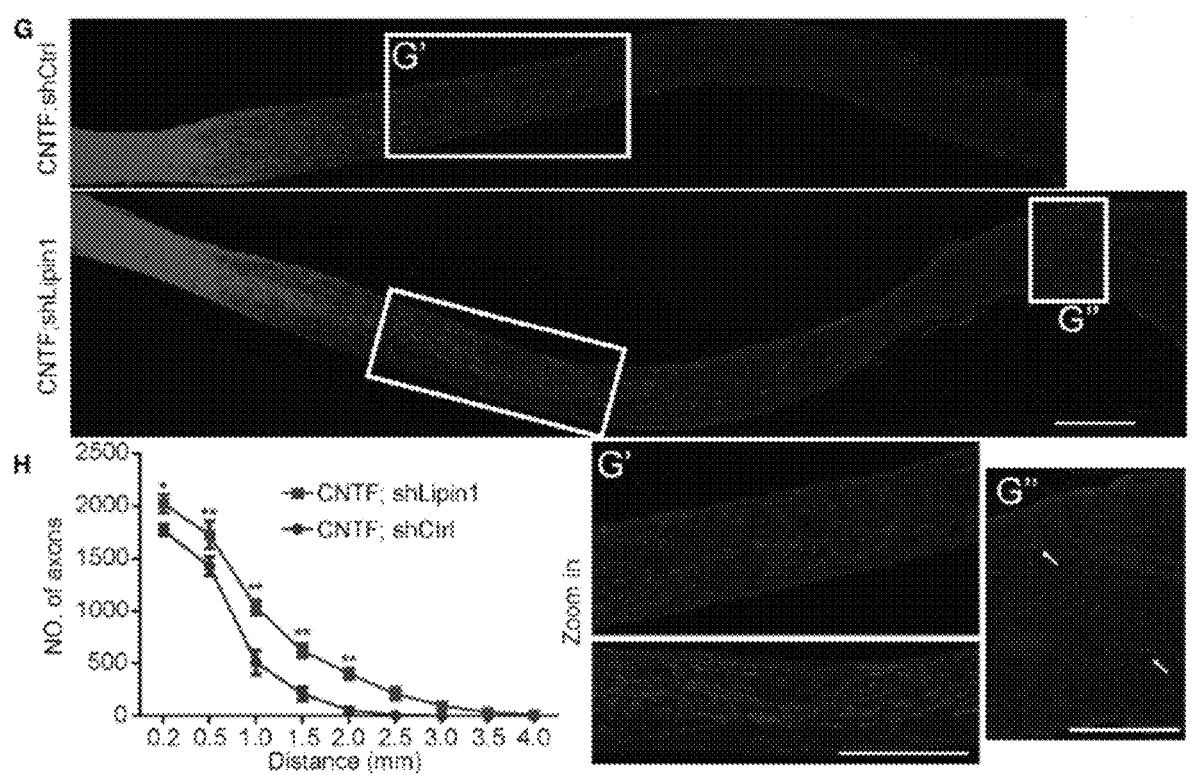

Consistent with the shRNA experiment, RGC survival was not affected by Lipin1 KO. The role of Lipin2, another member of the Lipin protein family, in axon regeneration was then studied. By doing qRT-PCR in sorted RGCs, it was observed that Lipin2 mRNA was not significantly changed after Lipin1 knockdown (KD). Then CRISPR was used to knock out Lipin2 in RGCs and to assess the growth effect after optic nerve crush. It was found that Lipin2 KO did not promote significant regrowth and did not further enhance axon regeneration induced by Lipin1 KD. The results suggested that Lipin2 does not compensate for the loss of Lipin1 in mediating axon regeneration. Furthermore, combining AAV-shLipin1 with AAV expressing ciliary neurotrophic factor (AAV-CNTF) achieved much more robust growth (FIGS. 1G-1H). Some axons even reached the optic chiasm within two weeks, which was rare after either treatment alone. Lipin1 KD may accelerate the speed of CNTF-induced regeneration. Lipin1 KD also enhanced axon regeneration induced by Pten KO.

To examine whether the extent of Lipin1 knockdown is correlated with the extent of axon regeneration, another AAV was made expressing Lipin1 shRNA2, different from the Lipin1 shRNA (SEQ ID NO: 1) used above. Lipin1-shRNA2 showed less knockdown efficiency compared to the Lipin1-shRNA. The axon regeneration induced by AAV-Lipin1-shRNA2 was also consistently less. Thus, through two approaches in vivo, it was demonstrated that neuronal Lipin1 functions as an intrinsic suppressor of axon regeneration.

Example 2

Lipin1 is Selectively Regulated by Aging and Injury in RGCs

Both aging and response to injury may mediate the intrinsic growth decline of CNS neurons (Belin et al., 2015; Byrne et al., 2014; Cho et al., 2015; Goldberg et al., 2002). It was postulated that lipid metabolism could be involved in the growth decline of CNS neurons. Lipin1 expression was examined in RGCs at different ages and after optic nerve injury. By performing immunostaining, it was found that Lipin1 protein in RGCs could hardly be detected in young mice but was elevated in adults (FIGS. 2A and 2B), suggesting that maturation may upregulate Lipin1. Interestingly, the vast majority of the αRGCs marked by the SMI32 antibody were Lipin1+. Over 80% of αRGCs expressed a lower level of Lipin1 (low Lipin1+), while the rest had a high expression level (high Lipin1+). After optic nerve crush, the percentage of high Lipin1+ αRGCs increased over threefold at 3 days post crush (dpc) (FIGS. 2C and 2D). In contrast, an evident change in the Lipin1 level was not detected in M1-M3 intrinsically photosensitive RGCs (ip-RGCs) by using Opn4-GFP mice, or RGCs labeled by TBR2 antibody. Tbr2 is expressed in a subset of RGC types that project to non-image-forming areas (Mao et al., 2014; Sweeney et al., 2014). Thus, maturation and axonal injury selectively regulate Lipin1 levels in RGCs.

Based on the results, a further study was conducted to determine whether the selective regulation of Lipin1 in injured αRGCs correlates with axon regeneration. αRGCs have been shown to regenerate their axons after Pten KO (Duan et al., 2015). To identify RGCs with axon regeneration induced by Lipin1 KD, fluorogold (FG) was injected into the optic nerve distal to the lesion site. Over 89% of the FG-labeled RGCs were αRGCs with SMI32 staining. Furthermore, it was observed that Lipin1 elevation in injured αRGCs was suppressed by either deleting Pten in RGCs or overexpressing AAV-CNTF in the retina, consistent with the notion that Lipin1 functions as an intrinsic inhibitor for RGCs to regenerate the axons.

Example 3

Lipin1 Suppresses Growth by its Phosphatidate Phosphatase Activity

Figures 3A, 3B, 3C:
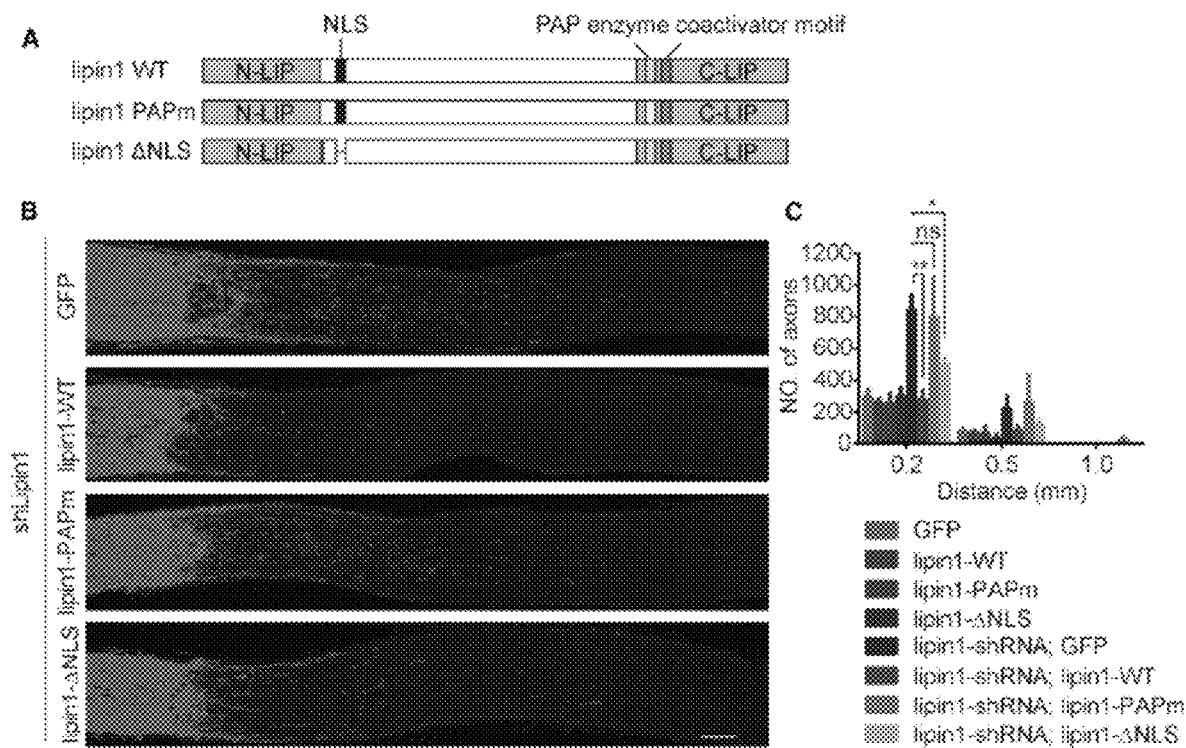
FIGS. 3A-3F depict (A) a schematic representation of the different lipin1 overexpression constructs used for the subsequent experiments; (B) sections of optic nerves from WT mice at 2 WPI, injected with AAV-lipin1-shRNA combined with AAV-GFP, AAV-lipin1-WT, AAV-lipin1-PAPm or AAV-lipin1-ΔNLS. Scale bar: 100 μm; (C) a graph showing the number of regenerating axons at different distances distal to the lesion site. ** P≤0.01, * P≤0.05, ANOVA followed by Tukey's test, n=5-6 mice; (D) a heatmap representing the alteration of lipidomes after lipin1 KD in cortical neurons (lipid species with the top 20 VIP are listed) (colors correspond to differences in relative abundance; and (E and F) graphs showing total TG and PC levels in cortical neurons after AAV-control or lipin1-shRNA treatment. ** P≤0.01, * P≤0.05, Student's t-test. Error bars indicate SEM.

Lipin1 has both PAP and transcription coactivator functions (Finck et al., 2006). An investigation was conducted to determine whether both functions were involved in Lipin1-dependent growth. The PAP catalytic motif (DxDxT) is present in the C-LIP domain of Lipin1, and conversion of the first or second aspartate residue in the DxDxT motif to glutamate completely abolishes PAP activity (Finck et al., 2006). The coactivator function can be decoupled from PAP function because mutations in the DxDxT motif abolish PAP activity but do not affect coactivator function (Finck et al., 2006). Thus, through AAVs, human WT Lipin1 (Lipin1-WT), Lipin1 with a PAP catalytic motif mutation (Lipin1-PAPm), and Lipin1 lacking a nuclear localization signal (Lipin1-ΔNLS) were expressed in RGCs with Lipin1 depletion (FIG. 3A). shRNA was designed to specifically knock down mouse Lipin1 and spare exogenous human Lipin1. Lipin1-WT but not Lipin1-PAPm suppressed axon regeneration to the level of control (FIGS. 3B and 3C), indicating that PAP activity rather than transcription coactivator function was essential. The result also confirmed that Lipin1 shRNA-induced regeneration was not due to potential off-target effects. Consistently, Lipin1-ΔNLS also significantly inhibited the growth effect caused by Lipin1 depletion (FIGS. 3B and 3C), suggesting that its nuclear function was not required. RGC survival was not significantly affected in the different groups. To examine the rescue effect in isolated neurons, an experiment was performed using adult DRG culture. Lipin1-WT and Lipin1-ΔNLS but not Lipin1-PAPm inhibited axon elongation in neurons induced by Lipin1 KD, consistent with the in vivo results. Thus, based on both in vitro and in vivo experiments, it was concluded that the PAP activity of Lipin1 plays a major role in inhibiting axon regeneration.

Example 4

Lipin1 Regulates Levels of Triglycerides and PLs in Neurons

Because PAP activity is critical for Lipin1-dependent axon growth, it was hypothesized that Lipin1 may control axon regrowth by regulating glycerolipid synthesis in neurons. In budding yeast and mammalian metabolic cells including adipocytes and hepatocytes, Lipin1, as a PAP enzyme, plays a major role in lipid homeostasis, especially in the balanced synthesis of TGs and PLs (Pascual and Carman, 2013; Siniossoglou, 2013; Zhang and Reue, 2017). Whether this lipid homeostasis is similarly regulated in neurons is not known. The hypothesis was tested in vitro. AAV-shLipin1 or AAV-shCtrl was added to cultured cortical neurons to achieve high KD efficacy. Glycerolipid levels were directly measured after eliminating glial cells by adding cytosine arabinoside (AraC) to the culture. To assess the change in the lipid profile in neurons after Lipin1 KD, E18 cortical neurons were with AAV-shCtrl or AAV-shLipin1. Lipid extraction of cortical neurons was analyzed by ultra-performance liquid chromatography-mass spectrometry (UPLC-MS) system. A non-targeted approach was employed to identify all of the molecules that differ between the two groups. Data were then analyzed by orthogonal partial least squares discriminant analysis (OPLS-DA) (Bylesjo et al., 2006).

Figures 3D, 3E, 3F:
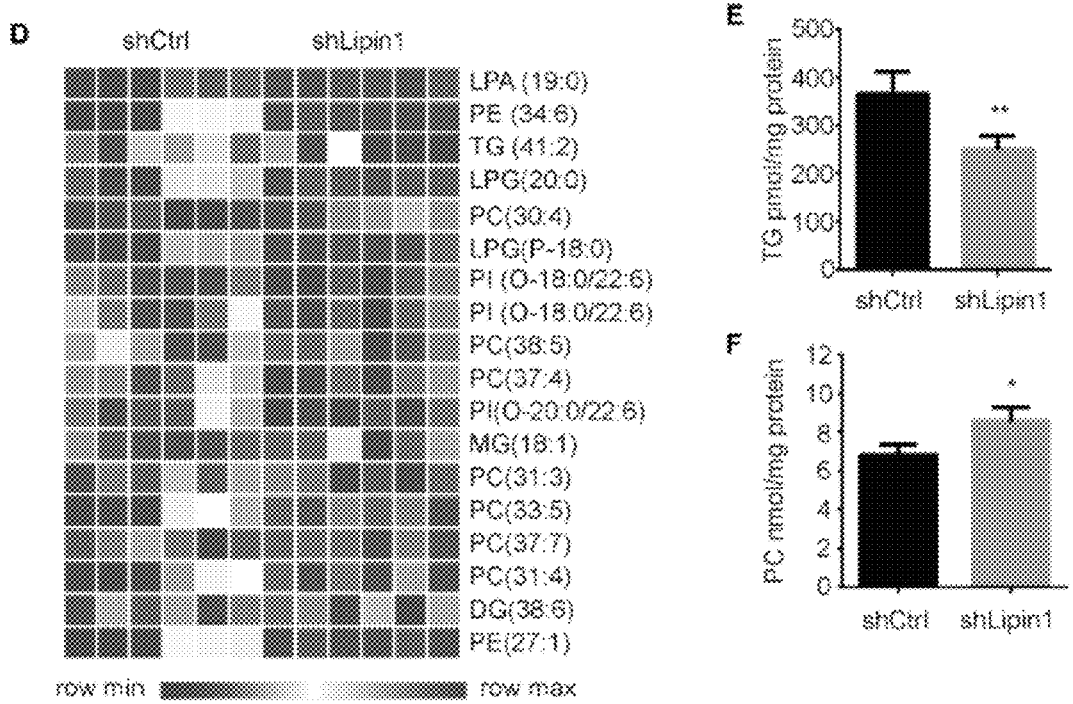

Among all the differential molecules, 57 molecules were identified as differential lipid species (p value<0.05 and variable importance for projection (VIP)>1) using lipid databases (FIG. 3D). DGs, TGs and PLs comprised 26% and 40% of all the differential lipids respectively, showing that the two metabolic pathways were highly regulated by Lipin1 in neurons. After Lipin1 depletion, the levels of TG(41:2) and TG(48:0), which were the most abundant among the eight identified TGs, decreased 18% and 28% respectively. The levels of the phosphatidylcholine (PC) lipids PC(30:4) and PC(33:5), which were the most abundant among the nine identified PCs, increased 17% and 15% respectively. The levels of the phosphatidylethanolamine (PE) lipids PE(36:4) and PE(37:3), which were the most abundant among the four identified PEs, increased 110% and 151% respectively. Cholesterol and free fatty acid were not significantly affected.

Because UPLC-MS might not identify all lipid molecular species, the total TG and PC levels were further measured by performing enzymatic hydrolysis assays. TG levels were decreased by 40% after Lipin1 depletion (FIG. 3E). Interestingly, PC levels were elevated by 26% (FIG. 3F). Thus, the two lipid assay methods consistently demonstrated that upon Lipin1 depletion, storage lipids were lower and membrane lipids were higher in neurons. Because injury triggers Lipin1 elevation in RGCs, the data on lipid changes after Lipin1 KD indicate that axotomy may program lipid metabolism to increase triglyceride and decrease PL production. This injury-triggered bias in lipid synthesis may contribute to the declined axon growth in CNS neurons. By depleting Lipin1, injured neurons may redirect two arms of the branch and shift lipid storage to membrane lipid production for axon regrowth.

Example 5

Increasing TG Storage Blocks Axon Regeneration

Figures 4A, 4B:
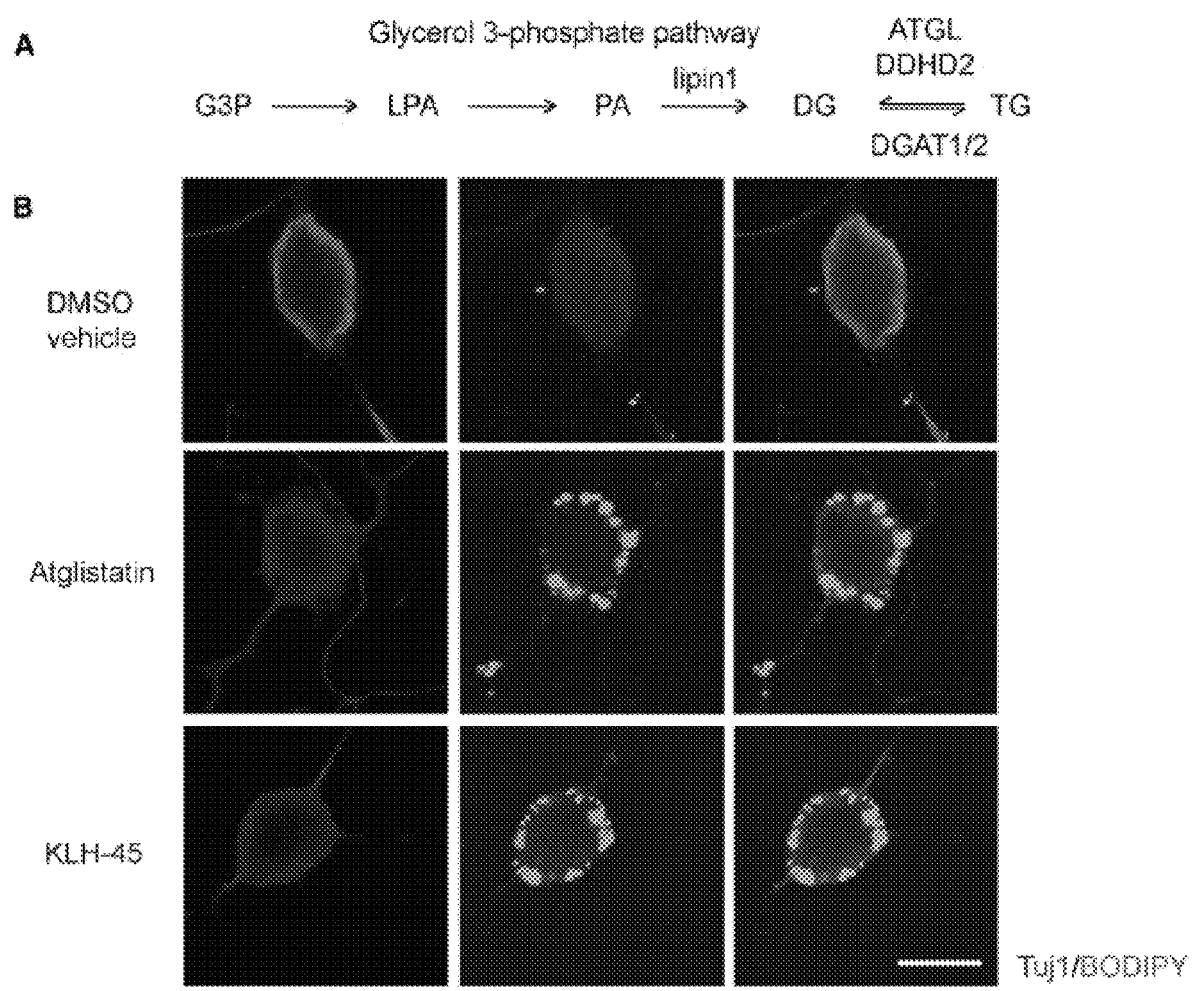
FIGS. 4A-4F depict (A) schematic showing the triglyceride metabolism pathway in mammals; (B) representative images of DRG neurons cultured with DMSO vehicle, Atglistatin or KLH-45 for three days. BODIPY staining was used to visualize lipid droplet distribution in neurons, (scale bar: 20 μm); (C) sections of optic nerves from Rosa26-Cas9 mice with lipin1-sgRNA injection at 2 WPI combined with AAV-control or Atgl shRNA (scale bar: 100 μm); (D) a graph showing the number of regenerating axons at different distances distal to the lesion site (** P≤0.01, ANOVA followed by Tukey's test, n=5-6 mice); (E) sections of optic nerves from Rosa26-Cas9 mice with lipin1-sgRNA injection at 2 WPI combined with AAV-control or Ddhd2 shRNA. Scale bar: 100 μm; and (F) a graph showing the number of regenerating axons at different distances distal to the lesion site. P≤0.05, ANOVA followed by Tukey's test, n=5-6 mice. Error bars indicate SEM.

Given that Lipin1 regulates the amount of TG in neurons, an investigation was conducted to determine whether neuronal TG metabolism was important for axon growth induced by Lipin1 depletion. TGs are often stored in lipid droplets, which can rarely be detected in neurons. The TG level in the brain is usually much lower than in other tissues (Csaki et al., 2014). Two TG lipases, adipose triglyceride lipase (ATGL) and DDHD2, are active in the brain (Etschmaier et al., 2011; Inloes et al., 2014), and they hydrolyze TGs to DGs and fatty acids (FIG. 4A). Knocking out Ddhd2 in mice causes large amounts of triglycerides to accumulate in the brain and lipid droplets to form in neurons (Inloes et al., 2014). Treating mice with a specific DDHD2 inhibitor elevates brain TGs within a few days (Inloes et al., 2014), indicating active TG hydrolysis in adult neurons.

Figures 4C, 4D, 4E, 4F:
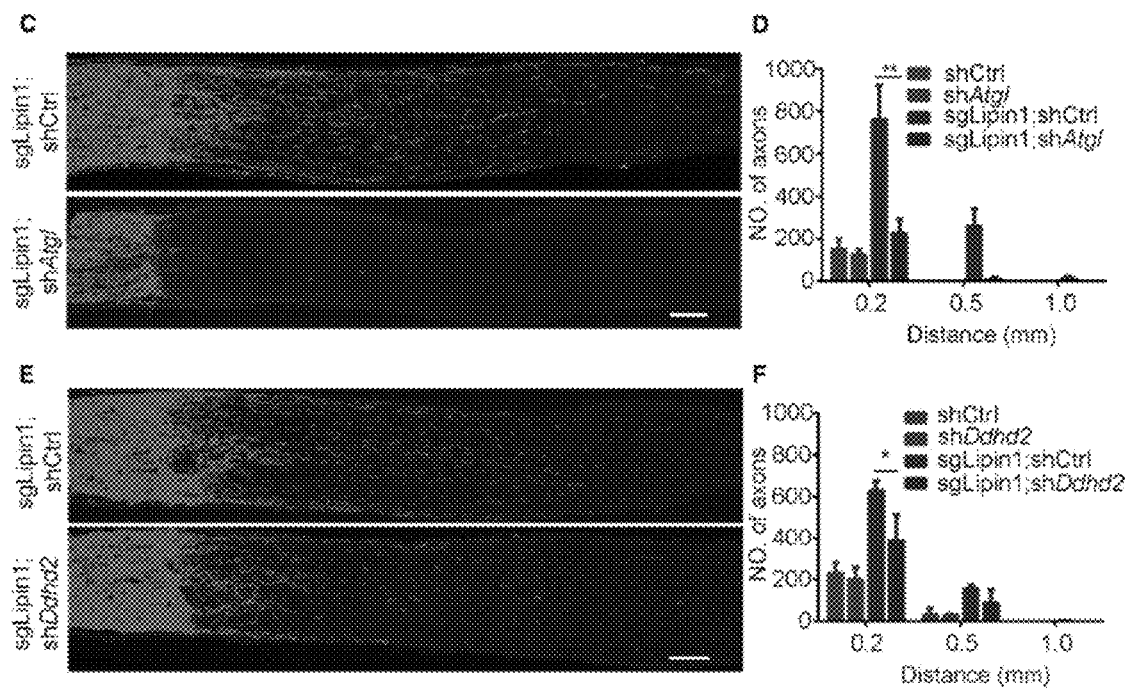

Experiments were performed to manipulate TG lipases in vitro. In cultured adult DRG neurons with vehicle treatment, lipid droplets were barely detected (FIG. 4B), consistent with the notion that neurons constantly turn over TGs with minimum storage. Either the ATGL inhibitor Atglistatin or the DDHD2 inhibitor KLH-45 dramatically increased TG storage in neurons, as shown by lipid droplet formation (FIG. 4B), indicating that these inhibitors effectively targeted TG lipases. Then, the function of TG lipases was examined in axon regeneration in vivo. AAVs were made carrying either Atgl shRNA (AAV-shAtgl) or Ddhd2 shRNA (AAV-shDdhd2) and the KD efficacy in vitro was verified. Then, these AAVs were injected into the eyes of mice with Lipin1 depleted in RGCs and the effect was examined two weeks after optic nerve crush. Expression of each individual virus and the coefficiency of two viruses were validated by whole-mount retina staining. AAV-shAtgl almost completely blocked axon regeneration (FIGS. 4C and 4D). AAV-shDdhd2 partially suppressed the regrowth (FIGS. 4E and 4F). RGC survival was not affected by either shRNA.

Whether increasing TG synthesis affects axon regeneration more generally was further examined. In mice injected with AAV-CNTF in the eyes or Pten deletion in RGCs, Atgl KD significantly suppressed the axon regeneration of the optic nerves. Thus, the data indicates that TG hydrolysis is indispensable to the axon regeneration induced not only by Lipin1 depletion but also by CNTF or Pten KO.

Example 6

Inhibiting TG Synthesis Promotes Axon Regeneration

Because it was demonstrated that TG hydrolysis was required, a further investigation was conducted to determine whether directly decreasing the level of neuronal TGs by restricting their biosynthesis can promote axon growth. In the final step of the glycerol phosphate pathway DGAT enzymes catalyze DGs into TGs. To assess the effect of blocking the DGAT enzyme, commercially available, DGAT1 inhibitors were used in culture. A-922500 (500 nM) and pradigastat (1 µM) were individually tested in a culture medium of DRG neurons. A combination of PF-06424439 (10 µM) and PF-046201101 (10 µM) was also tested in a culture medium of DRG neurons. An assay performed one day after the compound treatment demonstrated axon regrowth. The DGAT1 inhibitors enhanced the axon elongation of DRG neurons by 60%. Then, a KD experiment was performed by transfecting Dgat1 shRNA (shDgat1) targeting SEQ ID NO: 8, Dgat2 shRNA (shDgat2) targeting SEQ ID NO: 9 into DRG neurons. Compared with control shRNA, Dgat1 and Dgat2 shRNA both significantly boosted axon growth. Because axotomy increases Lipin1 expression in RGCs, a study was conducted to determine whether DGAT enzymes were also regulated by axonal injury.

Figures 5A, 5B, 5C, 5D:
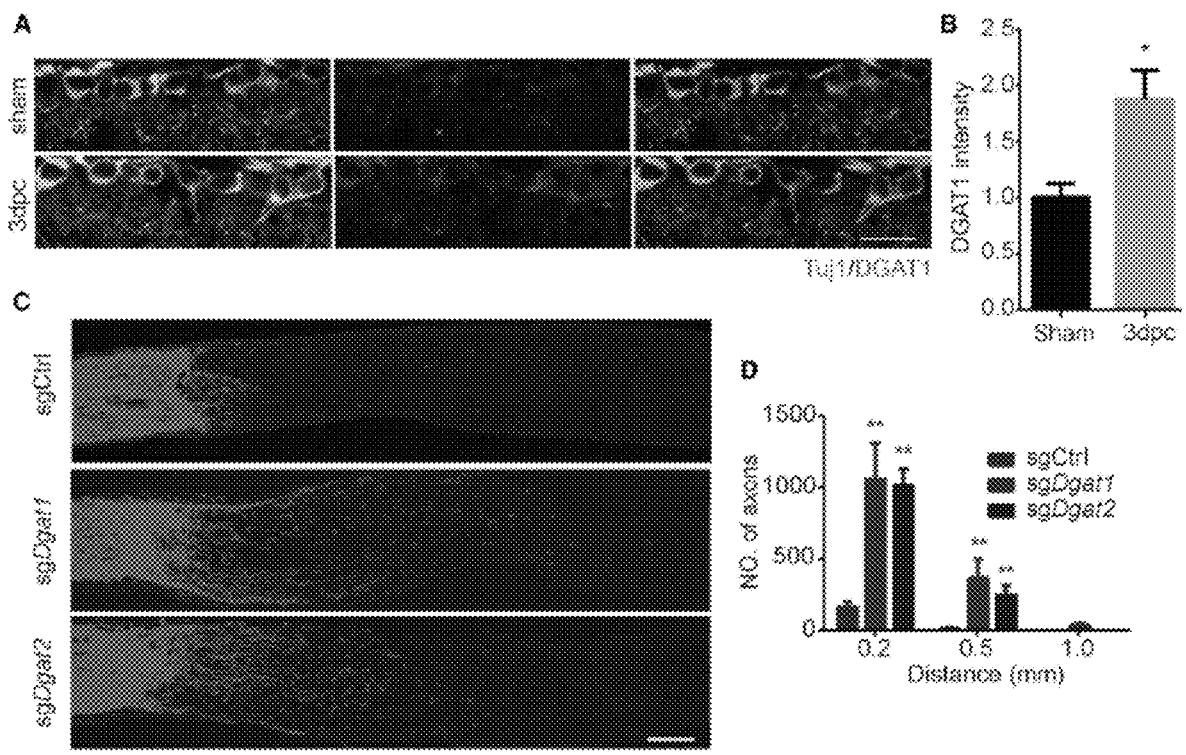
FIGS. 5A-5I depict (A) retinal sections from WT mice three days after injury or sham surgery collected and stained for Tuj1 and DGAT1 (scale bar: 50 μm); (B) quantification of relative fluorescence intensity of DGAT1 staining in RGCs. * P≤0.05, Student's t-test, n=5 mice; (C) sections of optic nerves from Rosa26-Cas9 mice at 2 WPI after the vitreous body was injected with AAV-control, Dgat1 or Dgat2-sgRNA (axons were labeled by CTB-FITC) (scale bar: 100 μm); (D) a graph showing the numbers of regenerating axons in (C) at indicated distances distal to the lesion site.  P≤0.01, ANOVA followed by Tukey's test, n=6 mice; (E and F) levels of individual TG and PC species normalized to the total protein from either Ctrl or Dgat1-shRNA group (the molecular species are indicated as the total number of carbons: the number of double bonds) ( P≤0.01, * P≤0.05, t-test, n=6); (G and H) graphs showing levels of total TGs or PC normalized to the total protein from either Ctrl or Dgat1-shRNA group. ** P≤0.01, * P≤0.05, ANOVA followed by Dunnett's test, n=6; and (I) a graph showing quantification of regenerated axons in injured optic nerves from Rosa26-Cas9 mice injected with AAV-Dgat1 or Dgat2-sgRNA at 2 WPI, combined with AAV-control or Atgl shRNA (the number of regenerating axons at the indicated distances distal to the lesion site are shown) (** P≤0.01, ANOVA followed by Tukey's test, n=6 mice; error bars indicate SEM).

Using the DGAT1 antibody, it was found that optic nerve injury elevated the level of DGAT1 in RGCs at 3 dpc (FIGS. 5A and 5B). Furthermore, DGATs were deleted in RGCs through CRISPR by injecting AAV-sgRNA against Dgat1 (AAV-sgDgat1) targeting both SEQ ID NO: 4 and SEQ ID NO: 5 or Dgat2 (AAV-sgDgat2) targeting both SEQ ID NO: 6 and SEQ ID NO: 7 into the eyes of Cas9 mice and assessed retinal axon regeneration after optic nerve injury. CRISPR induced genome editing was verified in vitro. Knocking out either Dgat1 or Dgat2 enhanced axon regeneration after injury without affecting RGC survival (FIGS. 5C and 5D). The lipid profile was then assessed in cultured neurons with Dgat1 KD to evaluate whether DGATs may affect glycerolipids in neurons.

Figures 5E, 5F, 5G, 5H, 5I:
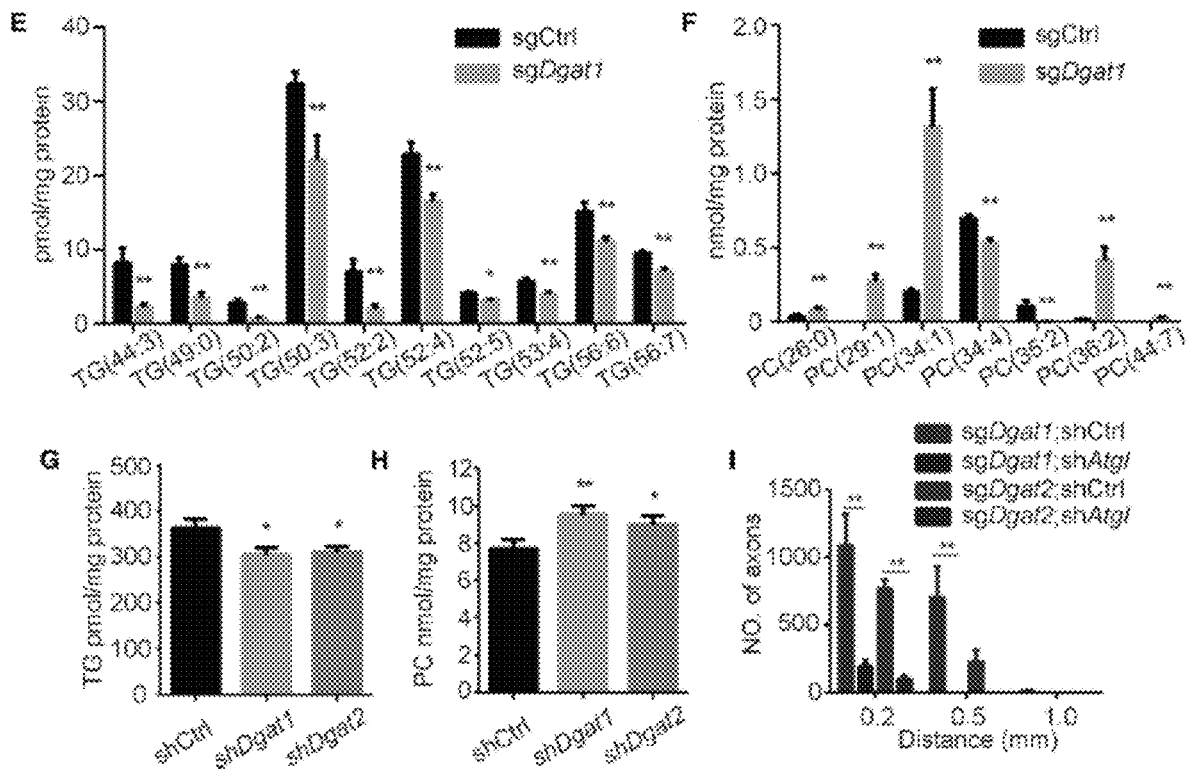

All identified TGs decreased after Dgat1 KD (FIG. 5E). Two abundant PC species PC(29:1) and PC(36:2) increased more than eightfold compared to the control shRNA group (FIG. 5F). The levels of TGs and PCs were then determined using lipid hydrolysis assays. Consistently, depleting DGAT1 or DGAT2 decreased the TG level in neurons (FIG. 5G). The PC content was increased (FIG. 5H). DGs, as a substrate for the DGAT reaction, are also a substrate for PL synthesis. The glycerol phosphate pathway may also provide DGs as an important precursor for PLs. It is believed that with Lipin1 elevation in injured neurons, neuronal depletion of DGAT1 or DGAT2 might divert DGs to the Kennedy pathway to increase PL synthesis. The DGs may come from PA dephosphorylation and TG hydrolysis.

A test was then conducted to determine whether TG hydrolysis was required for DGAT-dependent axon regeneration. AAV-shAtgl was injected into the eyes of mice with Dgat1 or Dgat2 deleted in RGCs and the optic nerve was examined two weeks after nerve crush. AAV-shAtgl dramatically suppressed the axon regeneration induced by knocking out either Dgat (FIG. 5I). The data indicate that inhibiting TG synthesis promotes axon regeneration possibly by providing DGs for PL synthesis through TG hydrolysis. Consistent with the notion that Lipin1 and DGAT1/2 are on the same lipid synthesis pathway, combining Lipin1 KD and Dgat1 KO did not further promote axon regeneration.

The data suggest that both Lipin1 and DGATs are important in determining the flux of lipids into TGs or PLs and the subsequent axon regeneration. Thus, axotomy drives up two essential enzymes of the glycerol phosphate pathway in neurons, suggesting the critical involvement of this lipid metabolic pathway in axon regeneration failure after injury.

Example 7

PL Biosynthesis Crucial for Axon Regeneration

Lipin1 depletion or mutation has been demonstrated to generate net increases in PC in several types of cells (Santos-Rosa et al., 2005; Zhang et al., 2012; Zhang et al., 2014). This result may be counterintuitive because DGs, the product of the PAP reaction, are a direct precursor of PC and PE. Several lines of evidence point to the possibility that a reduction in PAP activity elevates PA levels and subsequently PA may stimulate PCYT1, a critical enzyme for PC synthesis, leading to an increase in PC production (Craddock et al., 2015; Zhang et al., 2019). As two of the major building blocks of membranes, PC and PE are predicted to be essential during axon regrowth. However, disruption of Pcyt1b only generates a weak phenotype in axon branches and does not affect the axon elongation of sympathetic neurons in vitro (Strakova et al., 2011). The role of PL synthesis in axon regeneration especially in vivo has remained elusive. If Lipin1 depletion promotes regeneration by redirecting TG synthesis to PL synthesis in neurons, it was determined that the function of PL synthesis in axon regrowth should be evaluated more extensively.

The role of PL synthesis in axon regeneration induced by Lipin1 depletion was then assessed. The Kennedy pathway, the major biosynthetic pathway for de novo synthesis of PC and PE was studied (FIG. 6A) (Gibellini and Smith, 2010). The rate-limiting enzymes in the Kennedy pathway are CTP:phosphocholine cytidylyltransferase α (encoded by Pcyt1a), CTP:phosphocholine cytidylyltransferase β (encoded by Pcyt1b) for PC, and CTP:phosphoethanolamine cytidylyltransferase (encoded by Pcyt2) for PE. Several non-rate-limiting enzymes are also involved in PC synthesis, including Chka encoding choline kinase α, Chkb encoding choline kinase β, and Pemt encoding phosphatidylethanolamine N-methyltransferase. The function of each enzyme in axon regrowth was tested using shRNAs against Pcyt1a (shPcyt1), Pcyt1b (shPcyt1b), Pcyt2 (shPcyt2), Chka (shChka), Chkb (shChkb), and Pemt (shPemt) both in vitro and in vivo.

Figures 6A, 6B, 6C:
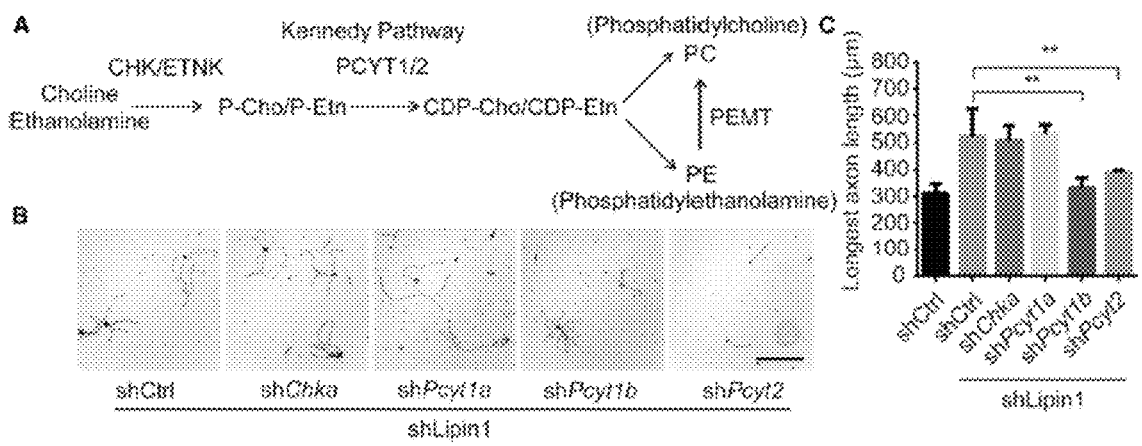
FIGS. 6A-6G depict (A) a schematic showing the PL synthesis pathways in mammals; (B) a graph representative images of replated neurons from the respective groups with Tuj1 staining (adult DRG neurons were dissociated and cultured with different AAV shRNA for 10 days, neurons were then replated and fixed 24 h later, and DRG neurites were visualized by Tuj1 staining) (scale bar: 400 μm); (C) a graph showing quantification of the length of the longest axon for each DRG neuron in (B) (three mice and 10-20 cells from each mouse were quantified in each group,  P≤0.01, ANOVA, followed by Tukey's test); (D) sections of optic nerves from Cas9 mice at 2 WPI after the vitreous body was injected with respective AAVs, axons were labeled by CTB-FITC (scale bar: 100 μm); (E) a graph showing the number of regenerating axons at the indicated distances distal to the lesion site.  P≤0.01, ANOVA followed by Tukey's test, n=6 mice; (F) sections of optic nerves from WT mice at 2 WPI after the vitreous body was injected with AAV-GFP, Pcyt1a, Pcyt1a-CA, or Pcyt2, axons were labeled by CTB-FITC (scale bar: 100 μm); and (G) a graph showing the number of regenerating axons at the indicated distances distal to the lesion site, ** P≤0.01, ANOVA followed by Tukey's test, n=6 mice (error bars indicate SEM).
Figures 6D, 6E, 6F:
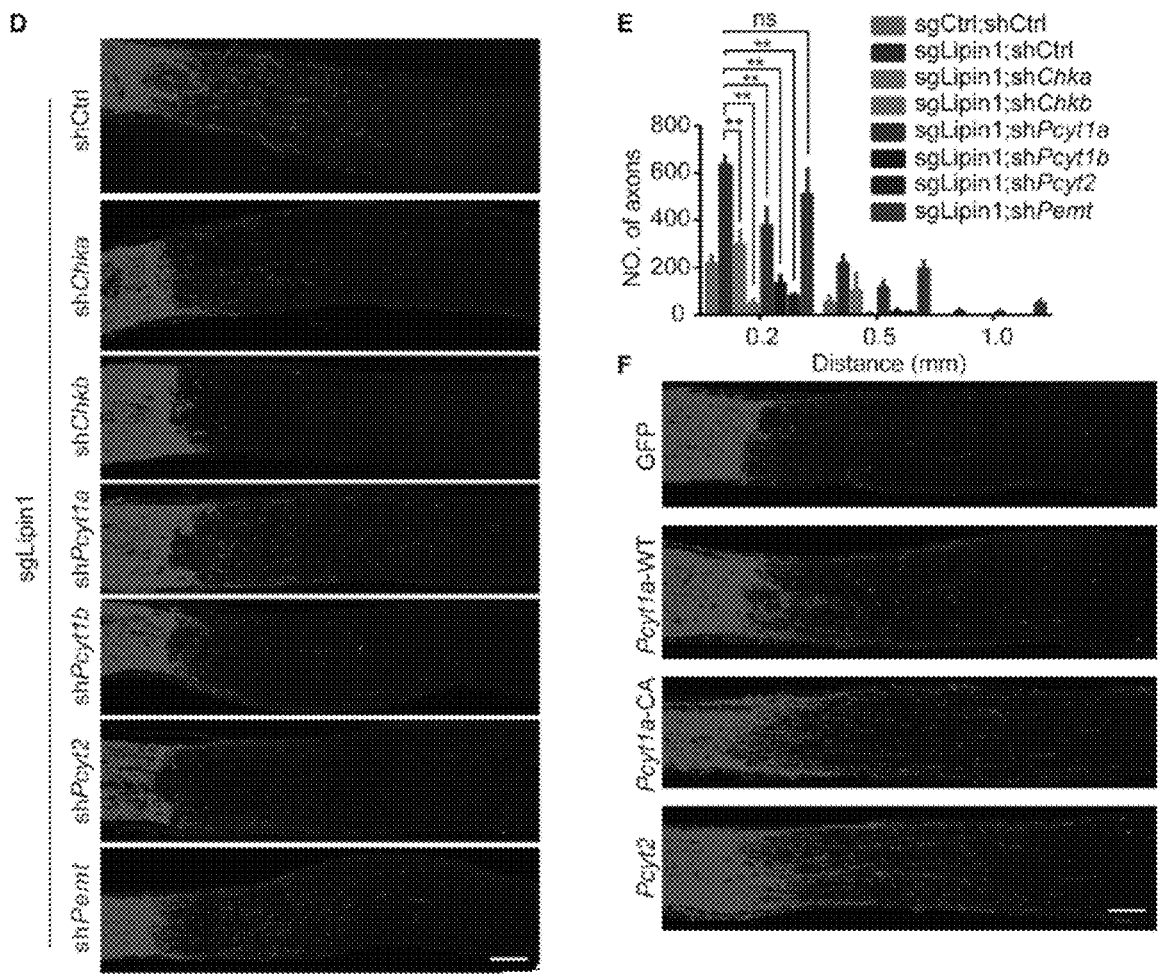

In DRG neurons, none of the tested shRNAs had an evident effect on axon elongation in WT neurons. Interestingly, axon growth enhanced by Lipin1 shRNA was completely reversed by Pcyt1b or Pcyt2 KD but not by Pcyt1a or Chka KD (FIGS. 6B and 6C). In the optic nerve injury model, a significant effect of any individual shRNA in WT mice was not found. In mice with Lipin1 depletion, Pcyt1b, Pcyt2, or Chkb KD almost completely blocked the enhanced axon regeneration (FIGS. 6D and 6E). Pcyt1a and Chka shRNA partially suppressed the regrowth (FIGS. 6D and 6E), whereas Pemt shRNA did not affect regeneration (FIGS. 6D and 6E). RGC survival was not affected by KD. In mice with Dgat1 KO in RGCs, Pcyt1a, Pcyt1b, Pcyt2, or Chkb KD significantly inhibited the axon regeneration. Whether PC synthesis affects axon regeneration more generally was then examined. In mice with AAV-CNTF injection into the eyes or Pten deletion in RGCs, Pcyt1b KD significantly suppressed the axon regeneration of the optic nerves. These results suggest that PC and PE synthesis mediated by the Kennedy pathway is indispensable to axon regeneration.

Figure 6G:
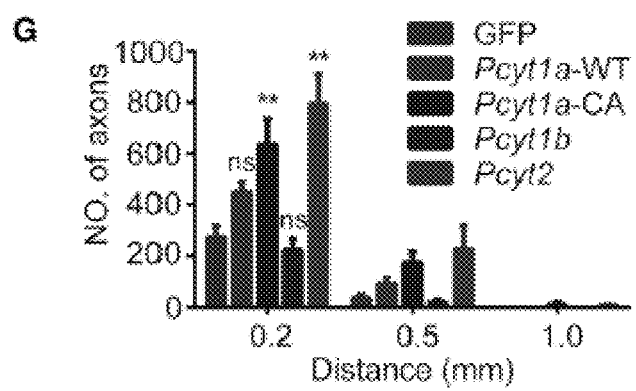

For the gain-of-function experiments, whether stimulating PL production by overexpressing Pcyt1a, Pcyt1b, and Pcyt2 in RGCs promotes axon regeneration was studied. For Pcyt1a, constitutively active Pcyt1 (Pcyt1a-CA) was included by removing the amphipathic C-terminal lipid-binding domain to prevent autoinhibition of the enzyme catalytic activity (Craddock et al., 2015). AAV carrying Pcyt1a, Pcyt1a-CA, Pcyt1b, or Pcyt2 was injected into the retinas of WT mice, which were subjected to optic nerve crush. Pcyt1a-CA and Pcyt2 overexpression enhanced axon regeneration at two weeks after injury (FIGS. 6F and 6G). Collectively, the results demonstrate that PL biosynthesis plays an essential role in axon regeneration induced by Lipin1 depletion.

It was demonstrated that αRGCs preferentially regenerate their axons after Lipin1 KD. To test the hypothesis that selective Lipin1 upregulation in αRGCs after injury may inhibit the axon regeneration by increasing TGs and decreasing PLs, the mRNA levels of Atgl, Pcyt1a, Pcyt1b in WT αRGCs and M1-M3 ipRGCs were compared. In Opn4-GFP mice with sham or optic nerve injury, micro-Ruby was injected into the optic nerve to label RGCs. Under the fluorescence microscope, RGCs labeled by micro-Ruby or GFP were manually isolated after retina dissociation and single-cell qRT-PCR was conducted. RGCs with high Spp1 expression were regarded as αRGCs (Duan et al., 2015). GFP was used to mark M1-M3 ipRGCs. It was found that Atgl and Pcyt2 were selectively down-regulated in αRGC but not in M1-M3 ipRGC. The results support that the glycerolipid metabolism is selectively regulated in RGCs after injury and mediates axon regeneration.

Example 8

TG Synthesis Inhibition Mediates Peripheral Axon Regeneration

As the PNS neurons spontaneously regenerate their axons and possess a stronger growth capacity than CNS neurons (Chandran et al., 2016), how the glycerol phosphate pathway is regulated in adult DRG neurons in vivo was examined. Three days after sciatic nerve injury in adult WT mice, immunostaining was performed to examine the levels of Lipin1 and DGAT1 proteins in DRG neurons. Lipin1 protein was detected in most neurons, and the level was maintained after injury. Knocking down Lipin1 in DRG neurons did not significantly enhance the spontaneous axon regeneration at three days after sciatic nerve crush. DGAT1 was found in both neuronal and non-neuronal cells.

In contrast to the injury-induced DGAT1 upregulation observed in RGCs, the level of neuronal DGAT1 was significantly decreased at 3 days after injury (FIG. 7A). The percentage of DGAT1+DRG neurons was reduced by ~50% compared with sham control (FIG. 7B). The staining of non-neuronal cells did not obviously change. This downregulation was not merely correlative because it was already shown that both DGAT1 inhibitors and KD can enhance DRG axon elongation in vitro. Because it was hypothesized that DGAT1 downregulation inhibits TG synthesis and directs TG-derived DGs to PL synthesis, the role of TG hydrolysis in DRG axon regeneration was further examined in vitro and in vivo.

In dissociated primary DRG neuron culture, TG lipase inhibitors—Atglistatin and KLH-45—significantly inhibited axon elongation (FIGS. 7C and 7D). Consistently, Ddhd2

KD in isolated DRG neurons suppressed axon elongation in culture, and as a positive control Lipin1 KD increased the axon length. Then, vehicle KLH-45, or KLH-45 combined with Atglistatin was systematically administered into WT mice. The sciatic nerve was then crushed, and the sensory axons were allowed to regrow for two days before examination. SCG10 was used as a marker to specifically label the regenerated sensory axons in the sciatic nerve as previously described (Chen et al., 2016; Shin et al., 2014). In the control mice, sensory axons robustly regenerated several hundred micrometers within two days. This spontaneous regeneration was modestly inhibited by KLH-45 alone and markedly suppressed by the combination of KLH-45 and Atglistatin (FIGS. 7E and 7F). Neuronal survival was not affected by the compounds. The results demonstrate that TG hydrolysis is required for peripheral axon regeneration. The differential regulation of the glycerol phosphate pathway in injured PNS and CNS neurons may contribute to the different regenerative capabilities.

Example 9

Inhibition of Triglyceride Synthesis Promotes Axon Sprouting after Pyramidotomy

In addition to regeneration of injured axons, collateral sprouting of uninjured axons is another mechanism that contributes to functional recovery following injury. Unilateral pyramidotomy was performed to assess the sprouting ability of corticospinal tract (CST) axons after lipin1 KD. AAV-control-shRNA or AAV-lipin1-shRNA was injected into the right sensorimotor cortex of postnatal day 1 (P1) WT mice, which then received left side pyramidotomy at 8 weeks old. The mice were terminated at 4 weeks post injury. Compared to the control group, mice with AAV-lipin1-shRNA injection showed significantly higher axon sprouting ability.

The present subject matter being thus described, it will be apparent that the same may be modified or varied in many ways. Such modifications and variations are not to be regarded as a departure from the spirit and scope of the present subject matter, and all such modifications and variations are intended to be included within the scope of the following claims.

We claim:

1. A method of promoting axon regeneration in a patient, comprising:
    administering a therapeutically effective amount of an inhibitor compound to the patient, wherein
    the inhibitor compound is a diglyceride acyltransferase inhibitor which comprises at least one of the following inhibitor compounds:

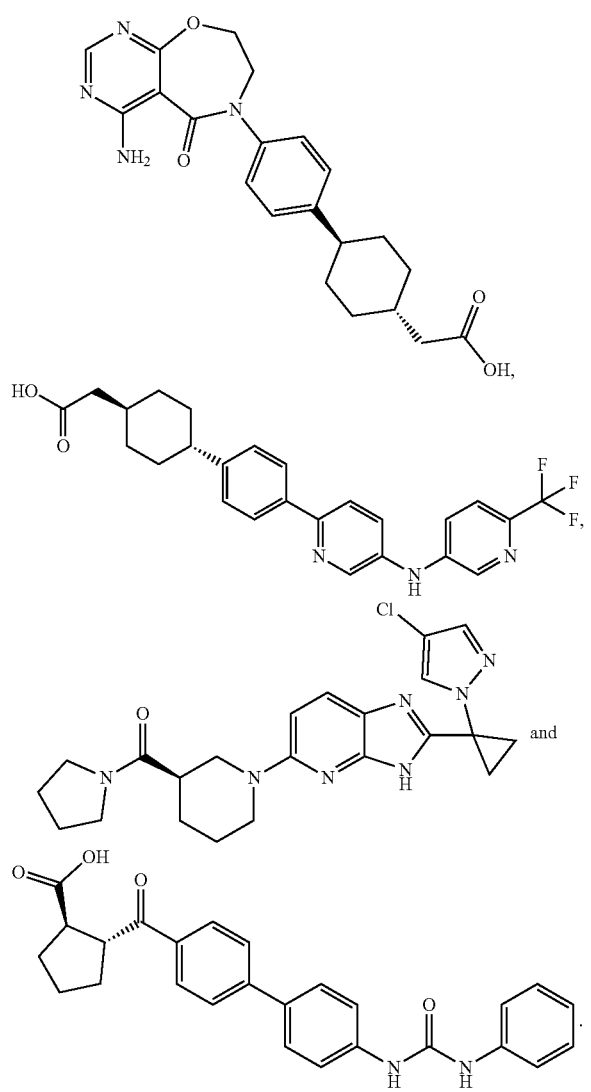

2. The method of claim 1, wherein the axons regenerated are sensory axons.

3. The method of claim 1, wherein the axons regenerated are optic or sciatic axons.

4. The method of claim 1, wherein more than one of the diglyceride acyltransferase inhibitor compounds are administered to the patient.

5. The method of claim 1, wherein the diglyceride acyltransferase inhibitor compounds comprise

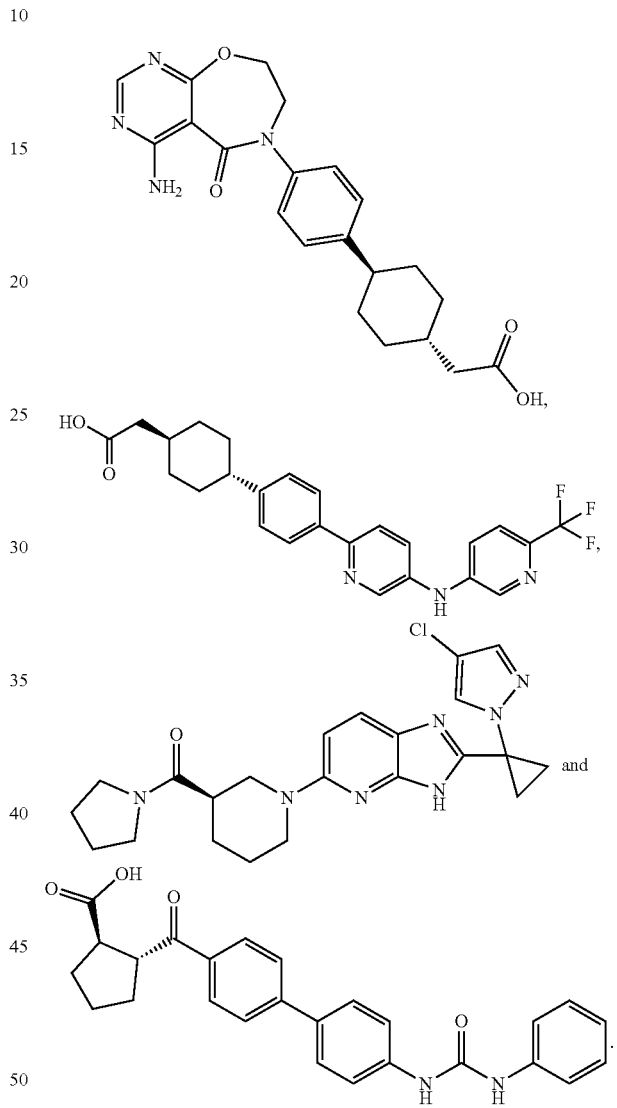

* * * * *

UNITED STATES PATENT AND TRADEMARK OFFICE
CERTIFICATE OF CORRECTION

PATENT NO. : 12,016,933 B2
APPLICATION NO. : 17/104714
DATED : June 25, 2024
INVENTOR(S) : Chao Yang, Xu Wang and Kai Liu Page 1 of 1

It is certified that error appears in the above-identified patent and that said Letters Patent is hereby corrected as shown below:

In the Claims

Claim 5, Column 36, Line 25, please delete the second structure and replace with the following:

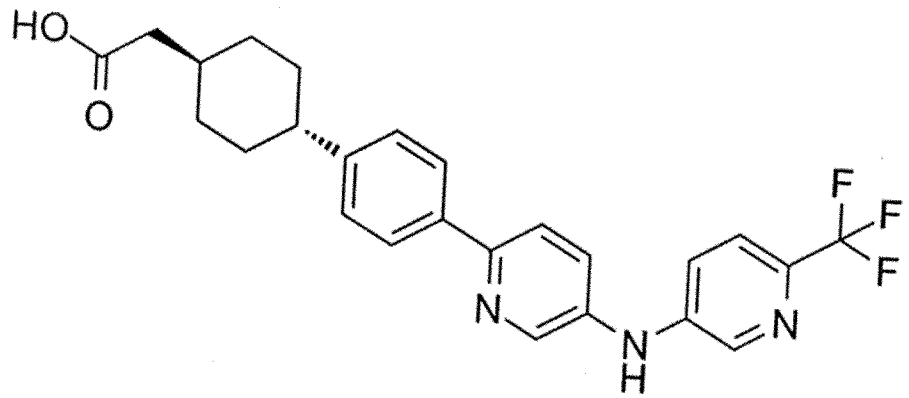

Signed and Sealed this
Tenth Day of September, 2024

Katherine Kelly Vidal
*Director of the United States Patent and Trademark Office*

SEQUENCE LISTING

```
<160> NUMBER OF SEQ ID NOS: 9

<210> SEQ ID NO 1
<211> LENGTH: 20
<212> TYPE: DNA
<213> ORGANISM: Artificial Sequence
<220> FEATURE:
<223> OTHER INFORMATION: Lipin1 shRNA

<400> SEQUENCE: 1
cggaactctg tagacagaat                                                   20

<210> SEQ ID NO 2
<211> LENGTH: 20
<212> TYPE: DNA
<213> ORGANISM: Artificial Sequence
<220> FEATURE:
<223> OTHER INFORMATION: Lipin sgRNA1

<400> SEQUENCE: 2
ggttcagaca atgaattacg                                                   20

<210> SEQ ID NO 3
<211> LENGTH: 20
<212> TYPE: DNA
<213> ORGANISM: Artificial Sequence
<220> FEATURE:
<223> OTHER INFORMATION: Lipin1 sgRNA2

<400> SEQUENCE: 3
gttcagacaa tgaattacgt                                                   20

<210> SEQ ID NO 4
<211> LENGTH: 19
<212> TYPE: DNA
<213> ORGANISM: Artificial Sequence
<220> FEATURE:
<223> OTHER INFORMATION: Dgat1 sgRNA1

<400> SEQUENCE: 4
ctcaactacg atgccccag                                                    19
```

```
<210> SEQ ID NO 5
<211> LENGTH: 21
<212> TYPE: DNA
<213> ORGANISM: Artificial Sequence
<220> FEATURE:
<223> OTHER INFORMATION: Dgat1 sgRNA2

<400> SEQUENCE: 5
gatcttgcag acgatggcac c                                              21

<210> SEQ ID NO 6
<211> LENGTH: 21
<212> TYPE: DNA
<213> ORGANISM: Artificial Sequence
<220> FEATURE:
<223> OTHER INFORMATION: Dgat2 sgRNA1

<400> SEQUENCE: 6
gatttggcct tccagagact g                                              21

<210> SEQ ID NO 7
<211> LENGTH: 21
<212> TYPE: DNA
<213> ORGANISM: Artificial Sequence
<220> FEATURE:
<223> OTHER INFORMATION: Dgat2 sgRNA2

<400> SEQUENCE: 7
gcccggagta ggcggcgatg a                                              21

<210> SEQ ID NO 8
<211> LENGTH: 20
<212> TYPE: DNA
<213> ORGANISM: Artificial Sequence
<220> FEATURE:
<223> OTHER INFORMATION: Dgat1 shRNA

<400> SEQUENCE: 8
gcccttcaag gatatggact                                                20

<210> SEQ ID NO 9
<211> LENGTH: 20
<212> TYPE: DNA
<213> ORGANISM: Artificial Sequence
<220> FEATURE:
<223> OTHER INFORMATION: Dgat2 sHRNA

<400> SEQUENCE: 9
gctacttccg agactacttt                                                20
```